United States Patent [19]
Brann

[11] Patent Number: 5,955,281
[45] Date of Patent: Sep. 21, 1999

[54] IDENTIFICATION OF LIGANDS BY SELECTIVE AMPLIFICATION OF CELLS TRANSFECTED WITH RECEPTORS

[75] Inventor: Mark Robert Brann, South Hero, Vt.

[73] Assignee: Acadia Pharmaceuticals, Inc., San Diego, Calif.

[21] Appl. No.: 08/965,947

[22] Filed: Nov. 7, 1997

Related U.S. Application Data

[60] Division of application No. 08/273,669, Jul. 12, 1994, Pat. No. 5,707,798, which is a continuation-in-part of application No. 08/091,694, Jul. 13, 1993, abandoned.

[51] Int. Cl.$^6$ .................................................. C12N 15/64
[52] U.S. Cl. ................................................ 435/6; 435/455
[58] Field of Search .................................. 435/6, 7.1, 72, 435/172.3, 252.3, 320.1, 455

[56] References Cited

U.S. PATENT DOCUMENTS 5,401,629  3/1995  Harpold et al. ............................. 435/6

OTHER PUBLICATIONS

Yamazaki et al. "A Deletion Mutation within the Ligand Binding Domain Is Responsible for Activation of Epidermal Growth Factor Receptor Gene in Human Brain Tumors". Jpn. J. Cencer Res. 81:773–779, Aug. 1990.

Hudson et al. "Identification and characterization of a regulated promoter element in the epidermal growth factor receptor gene". P.N.A.S. 87:7536–7540 Oct. 1990.

*Primary Examiner*—John Ulm
*Attorney, Agent, or Firm*—Cheryl H. Agris

[57] ABSTRACT

The invention is directed to a method for identifying substances acting as ligands for transfected receptors by using transfected markers to measure receptor/ligand interactions.

13 Claims, 21 Drawing Sheets

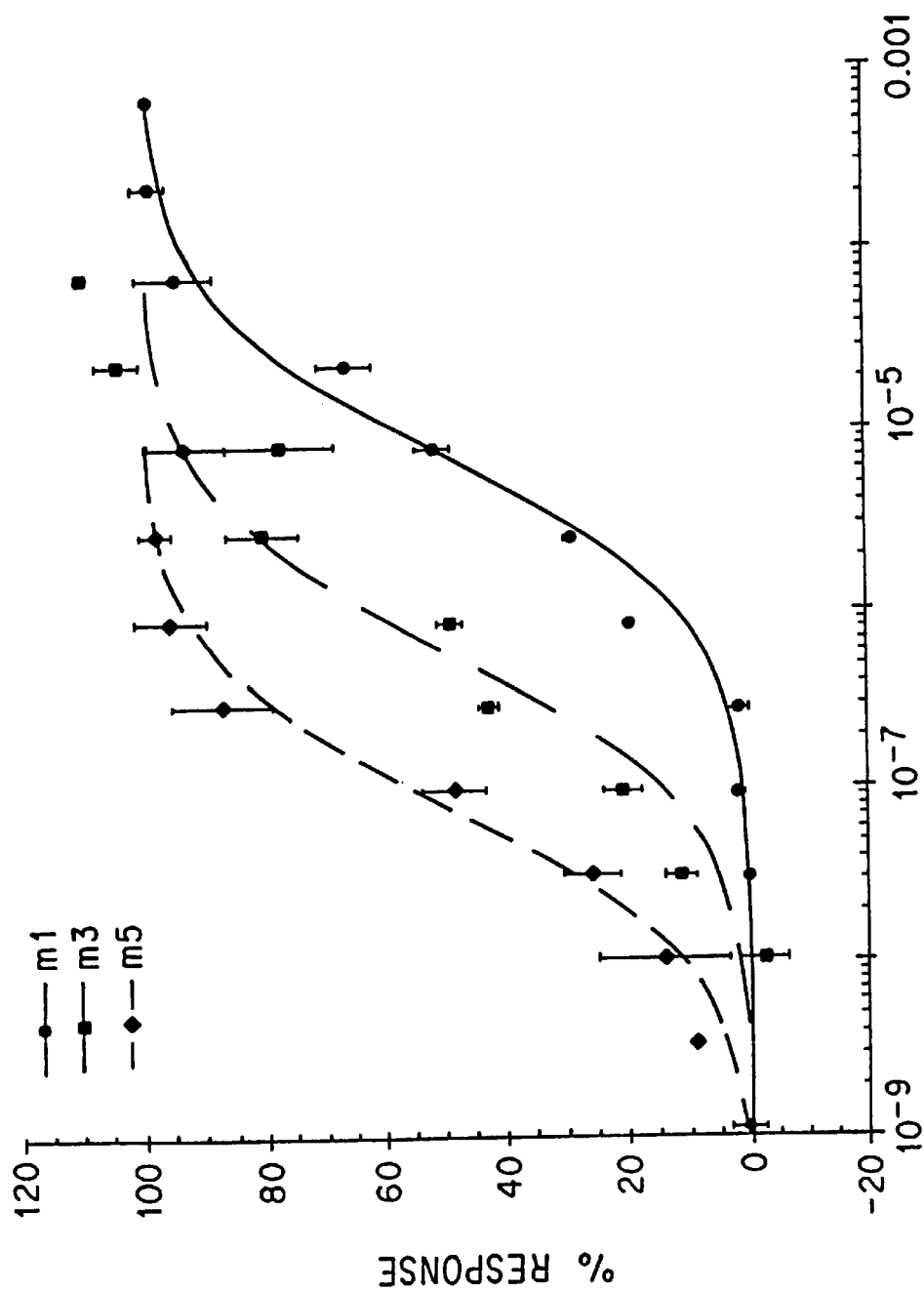

```
       L   Y   C   R   I   Y   R   E   T   E   K   R   T   K   D   L   A   D   L   Q
m5   leu tyr cys arg ile tyr arg glu thr glu lys arg thr lys asp leu ala asp leu gln val  —   —   —   —   —   —   —   —  ala  —   —   —   —   —   —  tyr  —   —
      —   —   —   —   —   —   —   —  glu  —  ala  —   —   —   —   —  glu  —   —
      —   —   —   —   —   —   —  val ala  —   —   —  —•  — val met  —   —   —   —
      —   —   —   —   —   —   —  ala —•  —  —• •—   —   —   —   —   —   —   —   —
      —   —   —   —   —   —   —   —   —   —   —   —   —   —   —   —   —   —  leu  —
      —  gly  —   —   —   —   —  val glu  —   —   —  asn  —   —   —   —   —   —
      —  trp  —   —   —  —•  —   —   —   —   —   —   —   —   —  ala  —   —
    —•   —  trp  —   —   —   —   —  val  —   —   —  —•  —   —   —   —   —   —
```

FIG.8A

```
      1   2   3   4   5   6   7   8   9  10  11  12  13  14  15  16  17  18  19  20
      .   .   x   .   .   .   0   .   .   .   .   x   .   .   .   0   .   x   .   0
m4  leu tyr ile his ile ser leu ala ser arg ser arg val his lys his arg pro glu gly
m2  leu tyr trp his ile ser arg ala ser lys ser arg ile lys lys asp lys lys glu pro m1  leu tyr trp arg ile tyr arg glu thr glu asn arg ala arg glu leu ala ala leu gln
m3  leu tyr trp arg ile tyr lys glu thr glu lys arg thr lys glu leu ala gly leu gln
m5  leu tyr cys arg ile tyr arg glu thr glu lys arg thr lys asp leu ala asp leu gln
```

FIG.8B

```
val      trp      met      gly val ala val thr      asn thr val met      tyr      leu
val      trp      met      gly val ala val thr      asn thr val          gly
         trp                   val ala val glu      ala thr asn          gly
         arg                       ala     val glu                       ala
         arg                       ala     ala                           glu
         gly                       asp     asp                           glu
                                   asp     asp
```

FIG.8C

```
his sto sto sto ser asp gln val lys gln asn sto arg sto gly sto val his
his sto ser gln ser asp asp val ile gln met his ser thr tyr pro gly cys
arg sto gly leu asn asn leu val     gly gly his ser arg val pro pro val
phe ser leu     val his     lys     arg     gly ala     gln     thr glu
pro cys ile     met         asp     val             ala
    phe                     asp     asp
    phe                             asp
                                    asp
```

FIG.8D

```
                            SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Leu Tyr Cys Arg Ile Tyr Arg Glu Thr Glu Lys Arg Thr Lys Asp Leu
1               5                  10                  15

Ala Asp Leu Gln
            20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Val Tyr Cys Arg Ile Tyr Arg Glu Thr Ala Lys Arg Thr Lys Asp Leu
1               5                  10                  15

Ala Tyr Leu Gln
            20

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Leu Tyr Cys Arg Ile Tyr Arg Glu Thr Glu Glu Arg Ala Lys Asp Leu
1               5                  10                  15

Ala Glu Leu Gln
            20

(2) INFORMATION FOR SEQ ID NO:4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO:4:

Leu Tyr Cys Arg Ile Tyr Arg Val Ala Glu Lys Arg Thr Lys Val Met
1               5                   10                  15

Ala Asp Leu Gln
            20

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Leu Tyr Cys Arg Ile Tyr Arg Ala Thr Glu Lys Arg Thr Lys Asp Leu
1               5                   10                  15

Ala Asp Leu Gln
            20

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Leu Tyr Cys Arg Ile Tyr Arg Glu Thr Glu Lys Arg Thr Lys Asp Leu
1               5                   10                  15

Ala Asp Leu Leu
            20

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Leu Tyr Gly Arg Ile Tyr Arg Glu Thr Val Glu Arg Thr Lys Asn Leu
1               5                   10                  15

Ala Asp Leu Gln
            20

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Leu Tyr Trp Arg Ile Tyr Arg Glu Thr Glu Lys Arg Thr Lys Asp Leu

```
                  1               5              10             15

Ala Ala Leu Gln
            20

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Leu Tyr Trp Arg Ile Tyr Arg Glu Thr Val Lys Arg Thr Lys Asp Leu
 1               5                  10                  15

Ala Asp Leu Gln
            20

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Leu Tyr Ile His Ile Ser Leu Ala Ser Arg Ser Arg Val His Lys His
 1               5                  10                  15

Arg Pro Glu Gly
            20

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Leu Tyr Trp His Ile Ser Arg Ala Ser Lys Ser Arg Ile Lys Lys Asp
 1               5                  10                  15

Lys Lys Glu Pro
            20

(2) INFORMATION FOR SEQ ID NO:12:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Leu Tyr Trp Arg Ile Tyr Arg Glu Thr Glu Asn Arg Ala Arg Glu Leu
 1               5                  10                  15

Ala Ala Leu Gln
            20
```

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Leu Tyr Trp Arg Ile Tyr Lys Glu Thr Glu Lys Arg Thr Lys Glu Leu
 1               5                  10                  15

Ala Gly Leu Gln
            20
```

IDENTIFICATION OF LIGANDS BY SELECTIVE AMPLIFICATION OF CELLS TRANSFECTED WITH RECEPTORS

This application is a divisional application of application Ser. No. 08/273,669, filed Jul. 12, 1994, now U.S. Pat. No. 5,707,798 which is a continuation-in-part of Ser. No. 08/091,694, filed Jul. 13, 1993, now abandoned.

FIELD OF INVENTION

The present invention relates to methods for identifying substances that act as ligands for cloned receptors, as well as a test kit for use in the methods.

BACKGROUND OF THE INVENTION

Many of the targets for pharmaceutical drug discovery are ligands for receptor proteins, many of which have recently been cloned and pharmacologically characterized. Now that a large number of receptors have been cloned, a major goal of the pharmaceutical industry is to identify ligands for these receptors by screening vast libraries of substances. Unfortunately, with available methods and technology, a major limitation in the drug discovery process is the time and expense required to screen these libraries against so many targets.

The first step in the characterization of ligand interaction with a cloned receptor is to express the receptor in a ligand sensitive form. While a few receptors can be expressed in easily manipulated model systems such as yeast and *E. coli*, the interactions of ligands with most receptors are influenced by postranslational modifications that are only present in mammalian cells, and many of these receptors require mammalian proteins to accurately transduce their biological effects. Thus for wide applicability, an assay system must be based on expression of cloned receptors in mammalian cells. The ability of ligands to interact with receptors can be evaluated by competition with a labeled ligand (eg. radionucleotide) for a binding site on the receptor. Such assays are popular because they involve relatively few steps. Also, since binding often does not require interaction with other cellular proteins, these assays are less sensitive to factors such as levels of expression of the receptor and the cellular environment. Recently, technology such as the Proximity Assay (Amersham Co) has further simplified these assays making automation and mass screening possible. Binding assays have many limitations: (i) For many technical reasons, binding assays are almost always performed in nonphysiological buffers. These buffers often markedly influence receptor pharmacology. (ii) Agonists and antagonists are not reliably discriminated in binding assays. (iii) Only binding sites for which labeled ligands are available can be studied. (iv) Since only modest levels of receptor (binding site) expression have been achieved in mammalian cells, propagation of receptors is a major expense in these assays. (v) The vast majority of labeled ligands are radioisotopes, the purchase, handling and disposal of which are major expenses.

To reliably discriminate between agonist and antagonist ligands, a response of the receptor must be measured. Responses to agonist activation of receptors are commonly measured as altered activity of various endogenous cellular proteins. Examples include measurement of second messengers such as cAMP (adenylyl cyclase), phosphoinositol metabolism (phospholipase c), tyrosine phosphorylation, and ion channels. All of these assays require the use of cells and/or cellular preparations that have a high degree of biological integrity, and these assays include many complex and expensive steps (Schlessinger and Ullrich, Neuron 9, 383 (1992); chapters in *Molecular Biology of G-protein-coupled receptors*, M Brann, ed., Birkhauser (1992)).

A strategy that has been used to avoid the time and expense of measurement of endogenous proteins is to express conveniently assayed marker proteins that can be controlled by activation of the receptor. For example, receptors that control levels of transcription factors can be assayed using markers whose expression is under the transcriptional control of these factors. While this approach has led to convenient assays of receptors that are known to function as controllers of transcription (eg. steroid/thyroid hormone receptors, Evans (WO 91/07488); Spanjaard et al. *Mol. Endocrinology* 7:12–16 (1993)), these assays have proven to have limited utility when applied to cell surface receptors, presumably because of the more modest transcriptional control that these receptors exert Other than the assays that are based on transcriptional control, no approach has been described to assay receptors via recombinant markers that can be conveniently measured.

Another approach is to express the receptors in specialized cells that have endogenous response mechanisms that allow convenient assay of ligand activation of the receptor. Two examples include the RBL cells and melanophores. In RBL cells, muscarinic receptors that stimulate phospholipase c enhance the release of the enzyme hexosaminidase (Jones et al., *FEBS Lett.* 289, 47 (1991)), a conveniently measured response. In melanophores (cultured pigment cells) cloned receptors that change cAMP levels alter cellular color, a response that is similarly easily measured (Potenza et al., *Anal. Biochem.* 206, 315 (1992)). The limitations of these assays are that only certain functional types of receptors can be measured. Also, while the assays are relatively convenient, there are limitations inherent in the endogenous responses and cells that are used.

When exposed to ligands, a wide diversity of receptors are able to alter the pH of the media that is used for cell culture. These pH changes are small in magnitude and require expensive instrumentation for measurement (Cytosensor, Molecular Dynamics Co.). This device is not compatible with other instruments that are used in mass screening (eg. use of a 96 well plate format) and because samples must be incubated within the instrument for several minutes, there is limited sample throughput.

A theoretical limitation inherent in all of the above assays is the inability to assay a given ligand against more than than a few receptors at the same time. For example, radioligand inding assays can only be multiplexed to the extent that different and distinguishable radioisotopes are available (eg. $^3$H versus $^{125}$I). Because of their limited dynamic range, incompatible assay conditions, and the fact that many receptors cannot be distinguished from one another based on their functional responses, second messenger responses, and most other biochemical effects of receptors, are not at all amenable to multiplexed assay. Similarly, the RBL assay, melanophore assay, and Cytosenor pH assays, are only applicable to assay of a single receptor at a time.

Another cellular response that is shared by many receptors is the ability to alter cellular growth. NIH 3T3 cells are a fibroblast cell line that has been extensively used to evaluate the activity of large diversity of gene products that control cell growth, and a number of receptors are able to control the activity of these cells when stimulated by individual ligands. Examples include nerve growth factor (NGF) which stimulates growth only when these cells have been transfected with trk A receptors (NGF receptor) (Cordon-Cardo et al., *Cell* 66:173–183 (1992); Chao, *Neuron* 9:583–593 (1992)), carbachol (a muscarinic agonist) stimulates cells transfected with certain muscarinic receptors (Gutkind et al., *Proc. Natl. Acad. Sci. USA* 88, 4703 (1991); Stephens et al., *Oncogene* 8, 19–26 (1993)), and norepinephrine stimulates cells transfected with certain alpha adrenergic receptors (Allen et al., *Proc. Natl. Acad. Sci. USA* 88, 11354 (1991)). After long-term stimulation with agonist ligands, the cells change a number of characteristics including cellular growth, loss of contact inhibition, and formation of macroscopic colonies called foci. The ability to induce foci in NIH 3T3 cells is a common characteristic of cancer-associated genes (oncogenes).

The ability of receptors and other gene products to stimulate growth and induce foci in NIH 3T3 cells correlates with the stimulation of individual second messenger systems. Trk A receptors stimulate tyrosine phosphorylation (tyrosine kinase receptor), and many other genes that stimulate tyrosine phosphorylation stimulate growth and focus production in NIH 3T3 cells (Schlessinger and Ullrich, *Neuron* 9, 383 (1992)) Certain muscarinic (Gutkind et al., *Proc. Natl. Acad. Sci. USA* 88, 4703 (1991)), adrenergic (Allen et al., *Proc. Natl. Acad. Sci. USA* 88, 11354 (1991)) and serotonergic (Julius et al., *Science* 244, 1057 (1989)) receptors that stimulate phospholipase c, also stimulate growth and focus formation in NIH 3T3 cells. In the case of the muscarinic receptors, the ability to stimulate foci and phospholipase c have exactly the same dose/response characteristics, suggesting that these responses may be used as assays for ligand interactions. Unfortunately, these assays offer few advantages to the approaches described above. Focus assays involve a response that requires at least two weeks of cell culture, and are confounded by qualitative changes in patterns of growth. Direct measurement of cellular growth has also been used to measure effects of ligands. The most commonly used assay is $^3$H-thymidine incorporation (Stephens et al., *Oncogene* 8, 1993, pp. 19–26). These assays are neither convenient nor inexpensive to perform.

SUMMARY OF THE INVENTION

It is an object of the present invention to provide an improved method for identifying ligands for cloned receptors.

It is another object of the present invention to provide a method for identifying ligands by simultaneous screening of compounds for activity at multiple cloned receptors.

It is a further object of the present invention to provide a method for measuring ligand concentrations by activity at cloned receptors.

It is still further object of the present invention to provide a method for employing recombinant signaling molecules to facilitate assay of ligands for additional cloned receptors.

It is a still further object of the present invention to provide a method to identify DNAs encoding receptors for ligands.

It is a still further object of the present invention to provide a method to identify mutant forms of receptors that have altered ligand dependence.

Accordingly, the present invention relates to a method of detecting a substance capable of acting as a ligand, the method comprising, (a) incubating, under conditions permitting cell amplification, cells transfected with DNA coding for a receptor capable of influencing cell amplification in response to a ligand, the cells comprising a marker of cell amplification, with a test substance which is a potential agonist or antagonist of the receptor, and (b) after a period of time sufficient to permit cell amplification, determining the presence or absence of amplification of cells containing the marker relative to cells not containing the marker.

In the method of the invention, a mixture of transfected and nontransfected cells will typically be present in step (a). When a test substance is added to the mixture, its ability to act as a ligand for the receptor of interest is determined in terms of its ability to confer a competitive advantage on the cells in the mixture which are expressing that receptor, relative to the cells which do not express the receptor. For example, as a rule, whether in vivo or in vitro, a cell population expressing a receptor will respond positively to a ligand by an overall enhancement of cell function, one aspect of which may be increase in growth rate, or loss of contact inhibition. Applying this observation to the practice of the present method, in vitro, all cells in a culture are essentially in competition with each other; when cells expressing the receptor of interest (transfected cells) are stimulated by a ligand, the enhanced function of the stimulated cells will permit them to flourish at the expense of the nonstimulated (nontransfected) cells. Thus, if the ligand being tested is an agonist of the receptor, the transfected cells in the mixture will be preferentially amplified in response to the agonist, in comparison with nontransfected cells. In other words, the transfected cell population will expand at a greater rate than will the nontransfected cells. In the present method, the transfected cells are distinguishable from the nontransfected cells in the mixed population by the presence of a marker in the transfected cells. Only when the transfected cells have been stimulated by the test ligand will the amplification signal (the marker) accumulate.

When the ligand is an antagonist, the action can be determined isimilarly, but in reverse, i.e., the cells containing the marker will be at a competitive disadvantage relative to the untransfected cells, the population of which will expand at a greater rate than the transfected cells. However, it is preferred that the assay for antagonists be conducted in the presence of an agonist, and the observed effect is a decrease in the amplification response brought about by the presence of the stimulatory ligand alone.

In another aspect, the present invention relates to a test kit for detecting a substance capable of acting as a ligand, the kit comprising, (a) frozen cells transfected with DNA coding for a receptor capable of influencing cell amplification in response to a ligand, the cells comprising a marker of cell amplification, (b) a medium for growing the cells, (c) a reagent for detecting the presence and quantity of the marker.

This test kit is useful for an embodiment of the present method in which the ligand activity of the test substance (or potentially a large number of test substances) is determined by means of a single receptor (the embodiment of method of the invention termed the Single Receptor Format below).

In a further aspect, the present invention relates to a test kit for detecting a substance capable of acting as a ligand, the kit comprising, (a) frozen cells transfected with DNA coding for a first receptor capable of influencing cell amplification in response to a ligand, the cells comprising a marker of cell amplification, (b) frozen cells transfected with DNA coding for a second receptor capable of influencing cell amplification in response to a ligand, the second receptor being distinct from the first receptor, the cells comprising a marker of cell amplification, (c) a medium for growing the cells, (d) a reagent for detecting the presence and quantity of the marker.

This test kit is useful for an embodiment of the present method in which the ability of the test substance (or potentially a large number of test substances) to act as a ligand to a specific receptor is determined by incubation of the test substance with at least two receptors, and potentially a large number of receptors simultaneously (the embodiment of method of the invention termed the Multiple Receptor Format below).

The present method represents a significant improvement over the screening assays of the prior art. Typically, the known "growth" assays require direct observation of increase of receptor expression, and are generally quantitiative, e.g., results are quantitatively determined by the incorporation of a radiolabeled reagent over a period of time as an indicator of cell growth. In many cases, such as focus assays, the indicator of cell growth, i.e., focus formation, sought in the assay may take several weeks to develop. In addition, it is common that distinct test cell and control cell lines have to be established before screening ligands can begin; consistency of results is difficult to achieve when working with separately cultured cell lines. Such assays are thus not only time consuming, but also quite costly. In contrast, the present assay is essentially qualitative: ligand-induced enchanced cell function of those cells expressing the receptor is determined by observation of amplification of the transfected cell population relative to the untransfected cell population from the same culture. The amplification is readily confirmed by the observation of the enhanced expression of a marker gene (e.g., an enzyme which produces a visually detectable product when reacting with its substrate) in the transfected cells. Separate control cell lines are not necessary, and the results are observable within a matter of a few days.

Definitions

In the present description and claims, the following terms shall be defined as indicated below.

A "test substance" is intended to include any drug, compound or molecule with potential biological activity.

A "ligand" is intended to include any substance that either inhibits or stimulates the activity of a receptor. An "agonist" is defined as a ligand increasing the functional activity of a receptor (i.e. signal transduction through the receptor). An "antagonist" is defined as a ligand decreasing the functional activity of a receptor either by inhibiting the action of an agonist or by its own activity.

A "receptor" is intended to include any molecule present inside or on the surface of a cell, which molecule may effect cellular physiology when either inhibited or stimulated by a ligand. Typically, receptors which may be used for the present purpose comprise an extracellular domain with ligand-binding properties, a transmembrane domain which anchors the receptor in the cell membrane and a cytoplasmic domain Which generates a cellular signal in response to ligand binding ("signal transduction"). In some cases, e.g. with adrenergic receptors, the transmembrane domain is in the form of up to several helical, predominantly hydrophobic structures spanning the cell membrane and part of the transmembrane domain has ligand-binding properties.

A "tyrosine kinase receptor" is intended to include any receptor that has intrinsic tyrosine kinase enzymatic activity.

A "tyrosine phosphatase receptor" is intended to include any receptor that has intrinsic tyrosine phosphatase enzymatic activity.

A "chimeric receptor" is intended to include any combination of two or more receptors where the functional "signal transducing" component of one receptor is fused to the ligand binding component of another receptor.

A "chimeric G-protein" is intended to include any combination of two G-proteins where the effector binding component of one G-protein is fused with the receptor binding component of another G-protein.

"Gq-i5" is defined as chimeric G-protein consisting of the G-protein Gq in which the five amino acids of the C-terminus are replaced with the C-terminal five amino acids of Gi.

"Gi" is intended to include any G-protein which when activated inhibits the enzyme adenylyl cyclase.

"Gq" is intended to include any G-protein which when activated stimulates the enzyme phospholipase c.

"Gs" is intended to include any G-protein which when activated stimulates the enzyme adenylyl cyclase.

A "G-protein-coupled receptor" is intended to include any receptor that mediates signal transduction by coupling with a guanine nucleotide binding protein.

A "G-protein" is defined as any member of the family of heterotrimeric, signal transducing guanine nucleotide binding proteins.

"Signal transduction" is defined as the process by which information from ligand binding to a receptor is translated into physiological change.

An "oncogene" is defined as any gene that is able to stimulate focus formation in NIH 3T3 cells in the absence of any ligand. These genes are often associated with cancerous tumors.

A "transcription factor" is defined as any substance that is able to alter the transcription of a given gene. These factors are often proteins that bind to regions of DNA which modify the activity of a promoter.

"Transfection" is defined as any method by which a foreign gene is inserted into a cultured cell.

A "marker" is defined as any substance that can be readily measured and distinguished from other cellular components. The marker may be the transfected receptor DNA, the transcribed receptor mRNA, an enzyme, a binding protein or an antigen.

A "cell" useful for the present purpose is one which has the ability to respond to signal transduction through a given receptor by cellular amplification.

An "aliquot" is defined as a portion of transfected cells provided on a solid support, e.g. a microtiter plate, test tube or microbead.

"Amplification" is intended to indicate the growth of receptor-transfected cells, in particular relative to the growth of non-receptor-transfected cells.

"Altered growth characteristics" is intended to indicate enhanced or decreased growth of receptor-transfected cells relative to non-receptor-transfected cells (background) cultured together with transfected cells. Cells incubated with an agonist will typically respond by enhanced growth or, in some cases, formation of foci on the culture plate. Cells incubated with an antagonist will typically respond by decreased growth.

Utility

The present invention is based on the ability of certain receptors to modulate cellular growth in a ligand-dependent fashion. The present method may be employed in two formats. In the Single Receptor Format which is particularly applicable to the detailed pharmacology of a single receptor, the ability of ligands to selectively induce the growth of receptor-transfected cells has been linked to induction of convenient markers. The Multiple Receptor Format which is applied to the assay of potential ligands against a large number of receptors simultaneously, utilises the ability of ligands to selectively induce markers that are unique to individual receptors in cultures which are mixtures of cells transfected with several receptors.

The Single Receptor Format allows the convenient assay of the interaction of agonist and antagonist ligands with individual receptors. The Multiple Receptor Format allows the convenient assay of the interaction of agonist and antagonist ligands with several receptors at the same time.

The Single Receptor Format involves very few steps; no expensive reagents; ability to quantitatively discriminate partial agonists, full agonists, and antagonists. Because the assay relies on transfections of recombinant receptor and marker DNA, the assay can be performed with a wide variety of receptors, markers and cell types. In addition to these properties, the Multiple Receptor Format represents the only method known to the inventor which can be applied to screening for ligand activity against large numbers of receptors simultaneously. Thus, the Multiple Receptor Format is particularly suitable for use in a drug screening programme wherein "hits" (that is, substances with ligand activity) may be identified quickly from among a large number of test subtances.

Receptor-based assays can be used to evaluate the concentrations of known ligands. The ligand to be measured may be incubated with transfected cells according to the present method. The major difference between chemical or immunologically based assays, and receptor-based assays is the fact that receptor-based assays measure the functional effect of the ligand. One application of this feature is in pharmacokinetic analysis of compounds. In these assays, receptor-based assays would detect active metabolites that may be missed by chemical or immunological techniques. Receptor-based assays would ignore inactive metabolites. Such data would be very useful in evaluating the role of occupancy of a given receptor in the therapeutic effect of test compounds. Another application of this approach is to identify the pharmacological properties of bodily fluids where drug history is unknown. One such application would be in illicit drug testing. In this case blood could be tested for ability to activate opiate receptors to determine if an idividual had consumed one of many opioids.

Another use of the present method could be to newly clone receptors to given ligands from cDNA libraries. Pools of cDNAs from a cDNA library may be screened for activation by a given ligand. Which cDNA in a given pool that encoded a responsive receptor would be identified by transfecting each cDNA in the library until the responsible receptor was identified. The strategy would be analogous to that illustrated in appended FIG. 11, except that unknown cDNAs are used for the transfections.

In a further use of the present method, libraries of a given receptor may be prepared by amplifying a specific gene from several individuals, tumors, tissues, or randomly mutated pools. These libraries of cDNAs can then be screened by transfecting pools of DNAs into cells, and growing the cells in the presence or absence of ligand. This strategy is likely to be particularly powerful when applied to identification of constitutively active versions of receptors (e.g. certain oncogenes)

DETAILED DESCRIPTION OF THE INVENTION

Single Receptor Format

In one embodiment of the present method, cells are transfected with DNA encoding a single receptor.

Transfection may be performed according to known methods. In general, a DNA sequence encoding a receptor may be inserted into a suitable cloning vector which may conveniently be subjected to recombinant DNA procedures. The vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the receptor should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the receptor in mammalian cells are the SV40 promoter (Subramani et al., Mol. Cell Biol. 1 (1981), 854–864), the MT-1 (metallothionein gene) promoter (Palmiter et al., Science 222 (1983), 809–814) or the adenovirus 2 major late promoter.

The DNA sequence encoding the receptor may also be operably connected to a suitable terminator, such as the human growth hormone terminator (Palmiter et al., op. cit.). The vector may further comprise elements such as polyadenylation signals (e.g. from SV40 or the adenovirus 5 Elb region), transcriptional enhancer sequences (e.g. the SV40 enhancer) and translational enhancer sequences (e.g. the ones encoding adenovirus VA RNAs).

The vector may further comprise a DNA sequence enabling the vector to replicate in the host-cell in question. An example of such a sequence (when the host cell is a mammalian cell) is the SV40 origin of replication.

The procedures used to ligate the DNA sequences coding for the receptor, the promoter and the terminator, respectively, and to insert them into suitable vectors containing the information necessary for replication, are well known to persons skilled in the art (cf., for instance, Sambrook et al., *Molecular Cloning: A Laboratory Manual*, Cold Spring Harbor Laboratory, Cold Spring Harbor, N.Y., 1989).

Cells which may be used in the present method are cells which are able to respond to signal transduction through a given receptor by cellular growth. Such cells are typically mammalian cells (or other eukaryotic cells) as cells of lower life forms generally lack appropriate signal transduction pathways for the present purpose. Examples of suitable cells are cells of the mouse fibroblast cell line NIH 3T3 (ATCC CRL 1658) which respond by growth to Gq and tyrosine kinase receptors as well as oncogenes (e.g. ras (cf. Barbacid, *Ann. Rev. Biochem.* 56, 1987, pp. 779–827) or p53), mutant G proteins (cf. Kalinec et al., *Mol. Cell. Biol.* 12, 1992, p. 4687); RAT 1 cells (Pace et al., *Proc. Natl. Acad. Sci. USA* 88, 1991, pp. 7031–7035) which respond to changes in cyclic AMP mediated by Gi and Gs receptors; and pituitary cells (Vallar et al., *Nature* 330, 1987, pp. 556–558) which also respond to changes in cyclic AMP mediated by Gi and Gs receptors.

Methods of transfecting mammalian cells and expressing DNA sequences introduced in the cells are described in e.g. Kaufman and Sharp, J. Mol. Biol. 159 (1982), 601–621;

Southern and Berg, J. Mol. Appl. Genet. 1 (1982), 327–341; Loyter et al., Proc. Natl. Acad. Sci. USA 79 (1982), 422–426; Wigler et al., Cell 14 (1978), 725; Corsaro and Pearson, Somatic Cell Genetics 7 (1981), 603, Graham and van der Eb, Virology 52 (1973), 456;

Neumann et al., EMBO J. 1 (1982), 841–845; and Wigler et al., Cell 11, 1977, pp. 223–232.

The DNA sequence encoding the receptor may encode a tyrosine kinase receptor, such as a colony stimulating factor 1 (CSF-1), platelet-derived growth factor (PDGF), epidermal growth factor (EGF), transforming growth factor (TGF), nerve growth factor (NGF), insulin, insulin-like growth factor 1 (IGF-1) receptor, etc.; a G-protein coupled receptor, such as a Gi-coupled, Gq-coupled or Gs-coupled receptor, e.g. a muscarinic receptor (e.g. the subtypes m1, m2, m3, m4, m5), dopamine receptor (e.g. the subtypes D1, D2, D4, D5)., opiate receptor (e.g. the subtypes μ or δ), adrenergic receptor (e.g. the subtypes α1A, α1B, α1C, α2C10, α2C2, α2C4), serotonin receptor, tachykinin receptor, luteinising hormone receptor or thyroid-stimulating hormone receptor (for further information on G-protein coupled receptors, vide M. Brann (ed.), *Molecular Biology of G-Protein Coupled Receptors*, Birhauser, Boston, 1992).

Receptors that couple to the G-protein Gs may be able to induce β-gal when expressed with a chimera between Gs and Gq (eg. Gq-s5). Alternatively, cells that respond to changes in Gs activity or cAMP could be used instead of the NIH 3T3 cells. Likely candidates are RAT 1 cells where cAMP is known to have significant effects on cellular growth (Pace et al. *Proc. Natl. Acad. Sci.* 88:7031–7035 (1991)), and certain pituitary cell lines where growth is sensitive to changes in the Gs pathway (Vallar et al. *Nature* 330:556–558 (1987)). A third possibility is to prepare chimeric receptors such that the ligand binding domain of a given Gs-coupled receptor is fused with the G-protein coupling domain of a Gq coupled receptor. Such chimeras have been reported for m1 muscarinic (Gq) and β-adrenergic receptors (Wong et al. *J. Biol. Chem.* 265:6219–6224 (1990)).

Several receptors have recently been identified that do not have intrinsic tyrosine kinase activity, but are able to stimulate the activity of tyrosine kinases endogenous to various cells including NIH 3T3 cells. One example is the GM-CSF receptor which induces foci in NIH 3T3 cells when activated by ligand (Areces et al. *Proc. Natl. Acad. Sci. USA* 90:3963–3967 (1993)). Like the tyrosine kinase receptors, these receptors may be assayed by the present method.

Recently, several receptors have been identified which have intrinsic tyrosine phosphatase activity. For use in the present method, tyrosine phosphatase receptors may be co-expressed together with a tyrosine kinase receptor. It is likely that these receptors could reverse tyrosine phosphorylation by tyrosine kinase receptors, and thus inhibit signals mediated by these receptors.

Transcription factors may be assayed by constructing vectors where the DNA binding target of a transcription factor is engineered to control the expression of a gene that stimulates cellular growth. Thus, if a ligand were to suppress the function of the transcription factor (or compete for the DNA binding site), expression to the growth controlling gene would be suppressed (Spanjaard et al. *Mol. Endocrinology.* 7:12–16 (1993)).

Receptors of the retinoic acid/steroid super family of receptors could be assayed by preparing chimeras between the ligand binding portions of these receptors, with proteins that stimulate cellular growth by acting as transcription factors. Chimeras between the glucocorticoid receptors and the oncogene c-fos allow glucocorticoids to stimulate foci in NIH 3T3 cells (Superti-Furga et al., *Proc. Natl. Acad. Sci. USA* 88:5114–5118 (1991)).

Many gene products that can induce ligand-independent growth may also be conveniently assayed by the present method. Many proteins that induce ligand-independent growth are mutant forms of receptors. Examples include forms of the trk A receptor, mutant forms of EGF receptors, the neu oncogene (Wong et al. *Proc. Natl. Acad. Sci. USA* 89: 2965–2969 (1992); Schlessinger et al. *Neuron* 9:383–391 (1992)). Also, many of these proteins are mutant forms of signal transducing proteins such as G-proteins (Barbacid *Ann. Rev. Biochem.* 56:779–827 (1987)). In principle, the advantage of the present method in this application is that general effects of compounds on growth can be distinguished from specific effects on the activity of the oncogene. This may be achieved by measuring overall cell growth and viability of the culture in parallel with the specific marker present in the transfected cells. Since the majority of cells are not transfected, general effects on cell growth must be nonspecific.

It is further envisaged that the receptor may be a ligand- or voltage-gated ion channel. Ligand-gated channels include subtypes of nicotinic acetylcholine receptors, GABA receptors, glutamate receptors (NMDA or other subtypes), subtype 3 of the serotonin receptor or the cAMP-regulated channel that causes cystic fibrosis. Voltage-gated ion channels include subtypes of potassium, sodium, chloride or calcium channels (cf. Lester, *Science* 241, 1988, p. 1057; Nicoll, *Science* 241, 1988, p. 545). To assay these channels, cells may be incubated under ionic conditionswhere activation (or inactivation) of the channel will yield a net change in ion flow. The cells could be genetically modified to increase the effect of changing intracellular ion channel concentration on cell amplification. For example, calcium channels may be assayed by co-transfecting the desired channel with an oncogene which is sensitive to calcium levels.

According to the present method, any agonist activity of the test substance may be determined by an enhanced effect of the receptor on growth of the receptor-transfected cells relative to a background of cells which have not been transfected with the receptor. Although an enhanced effect may be measured as either an increase or decrease in growth, the enhanced effect of the receptor in the presence of an agonist is most usually detected as enhanced amplification of the receptor-transfected cells.

According to the present method, any antagonist activity of the test substance may be determined by inhibition of the effect of the receptor on growth of the transfected cells relative to a background of cells which have not been transfected with the receptor. Although an inhibition of the effect may be measured as either an increase or decrease in growth, the inhibition of the effect of the receptor is typically detected as an inhibition of amplification of the receptor-transfected cells. In a particular embodiment, the test substance is incubated with the transfected cells in the presence of an agonist of receptor stimulation of cell amplification. Inhibition of cellular amplification by the agonist shows the presence of an antagonist.

In the transfected cells, the marker may be the transfected receptor DNA or the transcribed receptor mRNA. The presence of receptor DNA or mRNA may be determined by DNA amplification and/or hybridisation techniques.

For hybridisation purposes, DNA may be isolated from the cells and digested with a suitable restriction endonuclease. After digestion, the resulting DNA fragments may be subjected to electrophoresis on an agarose gel. DNA from the gel may then be blotted onto a nitrocellulose filter and hybridised with a radiolabelled oligonucleotide probe. The probe may conveniently contain a DNA fragment of the receptor gene (substantially according to the method of E. M. Southern, *J. Mol. Biol.* 98, 1975, pp. 503).

For amplification purposes, total mRNA isolated from the cells may be reverse transcribed to prepare a cDNA library. cDNA encoding the receptor may then be amplified by polymerase chain reaction (PCR) using oligonucleotide primers corresponding to segments of the gene coding for receptor in question and detected by size on an agarose gel. Amplified receptor cDNA may also be detected by hybridisation to a radiolabelled oligonucleotide probe comprising a DNA sequence corresponding to at least part of the gene encoding the receptor. This method is described by, e.g., Sambrook et al., supra.

The marker may also be an enzyme, a binding protein or an antigen. In this case, the cells are transfected with a DNA sequence encoding the marker in question.

Examples of enzymes useful as markers are phosphatases (such as acid or alkaline phosphatase), β-galactosidase, urease, glucose oxidase, carbonic anhydrase, acetylcholinesterase, glucoamylase, malate dehydrogenase, glucose-6-phosphate dehydrogenase, β-glucosidase, proteases, pyruvate decarboxylase, esterases, luciferase, alcohol dehydrogenase, or peroxidases (such as horseradish peroxidase).

To visualize enzyme activity in the present method, a substrate must be added to catalyse a reaction the end product of which is detectable. Examples of substrates which may be employed in the method according to the invention include o-nitrophenyl-β-D-galactopyranoside, 5-bromo-4-chloro-3-indolyl-β-D-galactopyranoside, chloronaphthole, o-phenylenediamine, 3-(p-hydroxyphenyl) propionic acid, luminol, indoxyl phosphate, p-nitrophenylphosphate, nitrophenyl galactose, 4-methyl umbelliferyl-D-galactopyranoside, $H_2O_2$/tetramethylbenzidine or luciferin.

Examples of binding proteins which may be used in the present method are avidin or streptavidin which may be detected with labelled biotin. Suitable sustances for labelling biotin may be fluorescent tags (e.g. fluorescein, phycoerythrin, phycocyanin) or marker enzymes (for instance one of the enzymes mentioned above). Other possible binding proteins are lectins, in articular plant lectins such as lentil lectin or wheat lectin. Lectins may be visualised by means of carbohydrates capable of binding to the respective lectins. Such carbohydrates may be labelled with the same substances as described above for biotin.

Examples of antigens which may be used in the present method are HLA or c-myc. Antigens may be visualised by means of labelled antibodies reactive with the respective antigens. The antibodies may be labelled with the same substances as those described above for biotin.

The marker is preferably an enzyme, in particular β-galactosidase encoded by the *E. coli* lacZ gene, or firefly luciferase. The DNA encoding the marker enzyme may be present on the vector which carries the receptor DNA, or it may be present on a separate vector which is then co-transfected with the vector carrying the receptor DNA.

In a particularly preferred embodiment of the single receptor format, the present method comprises (a) transfecting cells with DNA encoding the receptor and with DNA encoding a marker enzyme, (b) dividing the transfected cells into several identical aliquots, (c) incubating each aliquot with one or more test substances for a period of time sufficient to distinguish between stimulated and non-stimulated receptors, and (d) determining any change in cell growth by measuring marker enzyme activity in each aliquot.

To control for non-specific effects on cell growth in step (d), the amount of marker enzyme expressed by stimulated cells may be compared to the amount of a second and easily distinguishable marker enzyme expressed by non-transfected cells mixed into the culture before addition of the test substance. The advantage of using two different enzymes as markers according to the method of the invention is that the time needed to distinguish between stimulated and non-stimulated cells is relatively brief. There is no need to wait for several days until foci have formed on a culture plate and, in practical terms, the distinction can be made before it is ecessary to change the medium in the plates. Furthermore, if the enzyme reaction is chromogenic or luminescent, no separation of substrate is required before detection.

FIG. 2 is a schematic representation of a strategy for using cell growth as a convenient assay of ligand interaction with a single receptor. A high concentration of receptor DNA and a convenient marker DNA (eg. DNA coding for β-galactosidase) are used to transfect NIH 3T3 cells using calcium phosphate precipitation. Alternatively, the receptor and marker could be incorporated into the same plasmid. Using these conditions, a inority of cells would actually be transfected, and the majority of transfected cells will express both DNAs. In cultures that are grown in the absence of any ligand, all of the cells would have similar growth characteristics, and in theory the amount of marker found in the culture after a given time in culture would be proportional to the percentage of cells that were initially transfected with the marker. If the cells are incubated in the presence of a ligand that stimulates the receptor (agonist), the receptor-transfected cells will have a positive growth advantage relative to other cells in the culture. Since the majority of receptor-transfected cells also express the marker, then the amount of marker will be increased in the final cultures.

Multiple Receptor Format

In another embodiment of the present method, the cells are transfected with DNAs encoding two or more distinct receptors, each transfected cell expressing an individual receptor. This should be taken to mean that statistically each cell has been transfected with one individual receptor only. This may be obtained by using only small amounts of receptor DNA for transfection so that the DNA encoding any one particular receptor constitutes only a small percentage of the total DNA used for transfection, for instance by using carrier DNA or by transfecting the cells simultaneously with a number of different receptor DNAS. In the latter case, very few of the cells will be transfected with more than one receptor DNA although it cannot be excluded that other receptor DNAS may also be present in minor quantities in some of the cells. However, only the cells containing a receptor stimulated by the particular ligand added to the cells will be amplified according to the method (and thus become visible in the assay). As an alternative to this procedure, separate cell cultures may be transfected with each of the receptors and subsequently mixed before addition of the test substance(s).

Transfection procedures are otherwise as described above for the single receptor format. Likewise, the receptor types used for transfection are the same as indicated above. Because the strength of responses are related to signal transduction type, the best results would be obtained by testing receptors of the same class together, e.g. Gq-coupled receptors such as α1A, B and C adrenergic receptors, m1, m3 and m5 muscarinic receptors, S2 and 1c serotonin receptors; Gi-coupled receptors such as m2 and m4 muscarinic receptors, D2 and D4 dopamine receptors, 1e and 1d serotonin receptors; trk A, B and C receptors, EGF and PDGF receptors; adenosine receptors, α2 adrenergic receptor subtypes, somatostatin receptors, opiate μ and δ receptors; oncogenes such as ras, p53, neu oncogenes, or oncogenic forms of the trk, EGF, PDGF, etc., receptors.

Suitable markers are described above. However, it may be particularly advantageous to include different markers in the method of the invention such that cells expressing a given receptor also express a marker which is distinguishable from a marker expressed by cells transfected with another receptor (to make it easier to distinguish between the different receptors). To be distinguishable, enzymatic markers should not overlap in their substrate specificities (e.g. alkaline phosphatase and β-galactosidase). The substrates and detection mechanisms should therefore be selected for assays that can be distinguished (e.g. alkaline phosphatase to give a black reaction product and β-galactosidase to give a yellow reaction product). Alternatively, chromogenic and luminescent detection may be combined (e.g. β-galactosidase and firefly luciferase). In this case, the reactions may easily be distinguished because β-galactosidase yields a chromogenic product when reacted with o-nitrophenyl-β-D-galactopyranoside, while luciferase yields a luminescent product when reacted with luciferin. Luminescent reactions have the added advantage of yielding a labile product (light). Thus, several luminescent enzymatic reactions may be performed sequentially in the same reaction mixture.

In one particularly preferred embodiment of the multiple receptor format, the present method comprises
   (a) transfecting cells with DNAs encoding two or more distinct receptors, each transfected cell expressing an individual receptor, and with DNA encoding a marker enzyme,
   (b) dividing the transfected cells into several identical aliquots,
   (c) incubating each aliquot with one or more test substances for a period of time sufficient to distinguish between stimulated and non-stimulated receptors,
   (d) determining any change in cell growth by measuring marker enzyme activity in each aliquot, identifying active ligands by their ability to alter cell growth characteristics, and
   (e) identifying which receptor is activated by the ligand by subjecting each receptor to the method described above in steps (a)–(d) of the Single Receptor Format.

In another particularly preferred embodiment of the multiple receptor format, the present method comprises
   (a) transfecting cells with DNAs encoding two or more distinct receptors, each transfected cell expressing an individual receptor, and with DNA encoding a.marker enzyme,
   (b) dividing the transfected cells into several identical aliquots,
   (c) incubating each aliquot with one or more test substances for a period of time sufficient to discriminate between stimulated and non-stimulated receptors,
   (d) determining any. change in cell growth by measuring marker enzyme activity in each aliquot, identifying active ligands by their ability to alter cell growth characteristics, and
   (e) identifying which receptor is activated by the ligand by assaying the receptor DNA and/or mRNA by DNA amplification and/or hybridisation techniques.

In yet another particularly preferred embodiment of the multiple receptor format, the present method comprises
   (a) transfecting cells with DNAs encoding two or more distinct receptors, each transfected cell expressing an individual receptor, and with DNAs encoding two or more marker enzymes, such that cells expressing a given receptor express a marker which is distinguishable from a marker expressed by cells transfected with another receptor,
   (b) dividing the transfected cells into several identical aliquots,
   (c) incubating each aliquot with one or more test substances for a period of time sufficient to distinguish between stimulated and non-stimulated receptors,
   (d) determining any change in cell growth by measuring marker enzyme activity in each aliquot, identifying active ligands by their ability to alter cell growth characteristics, and
   (e) identifying which receptor is activated by the ligand by adding a substrate for each individual marker enzyme followed by assay.

These embodiments of the present invention are based on the principle that if instead of a series of mutant versions of a single receptor, multiple receptor types were transfected together and grown in the presence of a ligand, a large number of receptors and possibly also potential ligands could be tested simultaneouly, thus saving time in a drug screening programme. The receptor or receptors that the ligand is able to activate would lead to an amplification of cells that express that receptor, and thus the receptors that are activated by a given ligand could be identified in the culture, for instance by DNA amplification techniques.

A number of configurations of the Multiple Receptor Format are technically feasible. FIG. 10 presents the general concept of the Multiple Receptor Format. Here two receptors are transfected into NIH 3T3 cells using low concentrations of receptor DNA. Under these conditions a minority of cells would be transfected, and those that are transfected will normally only express a single receptor. Rarely, both receptors will be expressed in a given cell. If the culture is grown in the presence of ligand with agonist activity against R1 then R1 transfected cells will be amplified in the culture. For the cells where R2 was also expressed with R1 then some R2 will also be amplified. The amount of receptor amplification could be determined by having distinguishable markers expressed on each of the receptor plasmids, or alternatively by detecting the receptor mRNA of DNA directly by means of DNA amplification techniques.

One configuration of the Multiple Receptor (SEQ ID NO:1) Format is illustrated in FIG. 11. Here multiple receptors are co-expressed with a single marker. Activation of one or more of the receptors will result in induction of the marker, and identify the test ligand as having activity. Which of the receptors was activated could then be determined by screening against each receptor in isolation. This approach should have utility in mass screening of compounds for ligand activity against multiple receptor targets. An alternative approach to identifying which receptor was activated would be to measure receptor mRNA and/or DNA by DNA amplification techniques as illustrated in FIG. 14. The latter approach is likely to have considerable utility in the analysis of ligands as either antagonist or as inhibitors of receptors that have intrinsic activity (e.g., oncogenes).

BRIEF DESCRIPTION OF THE DRAWINGS

FIG. 6A illustrates the dose-response relationships of m1, m3 and m5 muscarinic receptors.

FIG. 8A illustrates the sequences within the mutated region of eight functional muscarinic receptors that were each isolated and sequenced from at least two different foci. The sequence of the wild-type m5 receptor is indicated at the top (single and three letter codes) followed by the mutant sequences (SEQ ID NO:2–9). Base changes that did not alter the encoded amino acid are indicated by an (*), and predicted amino acid changes are indicated with conservative substitutions in plain type and nonconservative substitutions in bold type. Twenty additional unique sequences were isolated from independent foci. For the 28 mutant receptor sequences, an average of 2.4 amino acid changes were observed/receptor.

FIG. 8b illustrates a comparison of the sequences of the five wild-type muscarinic receptor subtypes (SEQ ID NO:10–13). Shading indicates identity or conservative substitutions with respect to the sequence of the m5 receptor (SEQ ID NO:1). Positions where only identical or conservative substitutions are tolerated for all five of the receptor subtypes are indicated by an (°). Positions where nonconservative substitutions that are not related to the functional classification of the receptors (m2/m4 versus m1/m3/m5) are indicated by an (x). Positions where at least the PI-linked muscarinic receptors (m1/m3/m5) are conserved are indicated by an (0). Positions where the substitutions are predictive of functional classification are indicated by an (*, m1/m3/m5 conserved, nonconserved versus m2/m4, and m2/m4 conserved). Boxed residues are conserved with respect to positions where no nonconservative substitutions were identified in the mutated receptors (indicated below the positions indicated in part C).

FIG. 8c illustrates a compilation of all amino acid substitutions that were identified in at least two independent foci. Amino acid substitutions are listed below the corresponding amino acid substitution listed in B. Amino acid substitutions are listed once for each independent receptor. Positions of amino acid changes that were observed in at least two foci are indicated below the position of the corresponding wild-type amino acid. These amino acid changes are compiled from the 28 independent mutant receptors isolated from the 675 recombinant library. Positions where no nonconservative substitutions were isolated are boxed. Amino acids where the other muscarinic receptors are conserved with respect to m5 are also included in these boxes.

FIG. 8d illustrates a compilation of amino acid substitutions observed in 17 clones selected at random from the mutant receptor library expressed in E. coli. (prior to transfection and selection by transformation of NIH 3T3 cells). An average of 4.2 amino acid substitutions were observed per mutant receptor. The presence of stop codons is indicated (Sto). Conservative substitutions are defined as members of the following groups: S(Ser), T(Thr), P(Pro), A(Ala), and G(Gly); N(Asn), D(Asp), E(Glu), andQ(Gln); H(His), K(Lys), andR(Arg); M(Met), I(Ile), L(Leu) and V(Val); F(Phe), Y(Tyr) and W(Trp); or C(Cys).

The present invention is further illustrated in the following examples which are not to be regarded as limiting in any way to the scope of the invention as claimed.

EXAMPLES
A General protocol for the Single Receptor Format

Cultures of NIH 3T3 cells (available from the American Type Culture Collection, as ATCC CRL 1658) were prepared to 50–60% confluence. On day one cells were trypsinized, spun down and plated at $1 \times 10^6$ cells/10 cm plate in 10 ml Dulbecco's Modified Eagle's Medium (DMEM), 10% calf serum (yield 3–4 10 cm plates from one 175 cm² flask). On day 2, cells were transfected using the calcium phosphate precipitation procedure of Wigler et al. Cell 11: 223–232 (1977). For each plate 5 μg receptor DNA, 5 μg β-gal DNA (β-gal, pSV-β-galactosidase, Promega), 20 μg salmon sperm DNA, 62.5 μl 2.0M $CaCl_2$, were brought.to 0.5 ml with $H_2O$. The DNA solution was added dropwise to 0.5 ml 2× HEPES-buffered saline (280 mM NaCl, 10 mM KCl, 1.5 mM $Na_2HPO_4$—$2H_2O$, 12 mM dextrose, 50 mM N-(2-hydroxyethyl)piperazine-N'-(2-ethanesulfonic acid) (HEPES), pH 7.05) while gently mixing with air bubbles. On day three plates were washed with HANK's balanced saline solution (HBSS) and 10 ml DMEM+10% calf serum was added. On day four the cells were trypsinized, spun down and resuspended in 10 ml (DMEM+10% calf serum). 100 μl of the suspension was added to each well of a 96 well plate. A 2× concentration of the test compound in 100 μl DMEM (10% calf serum) was added to each well. Cells were incubated with test substances for three to five days without changing media. A modified method of Lim and Chae, Biotechniques 7:576–579 (1989) was used to assay β-gal. On the day of β-gal assay, the media were aspirated and the wells rinsed with 100 μl phosphate-buffered saline (PBS). 200 μl of PBS with 3.5 mM o-nitrophenyl-β-D-galactopyranoside and 0.5% Nonidet P-40 (Sigma) was added to each well and incubated for 4 hrs at room temperature. β-gal responses were linear for several hrs. The absorbance of each well was determined by means of a plate reader (BioTec) set to ~405 nm.

Example 1
β-galactosidase Activity in Cells Transfected with the trk A Receptor

Figure 3A:
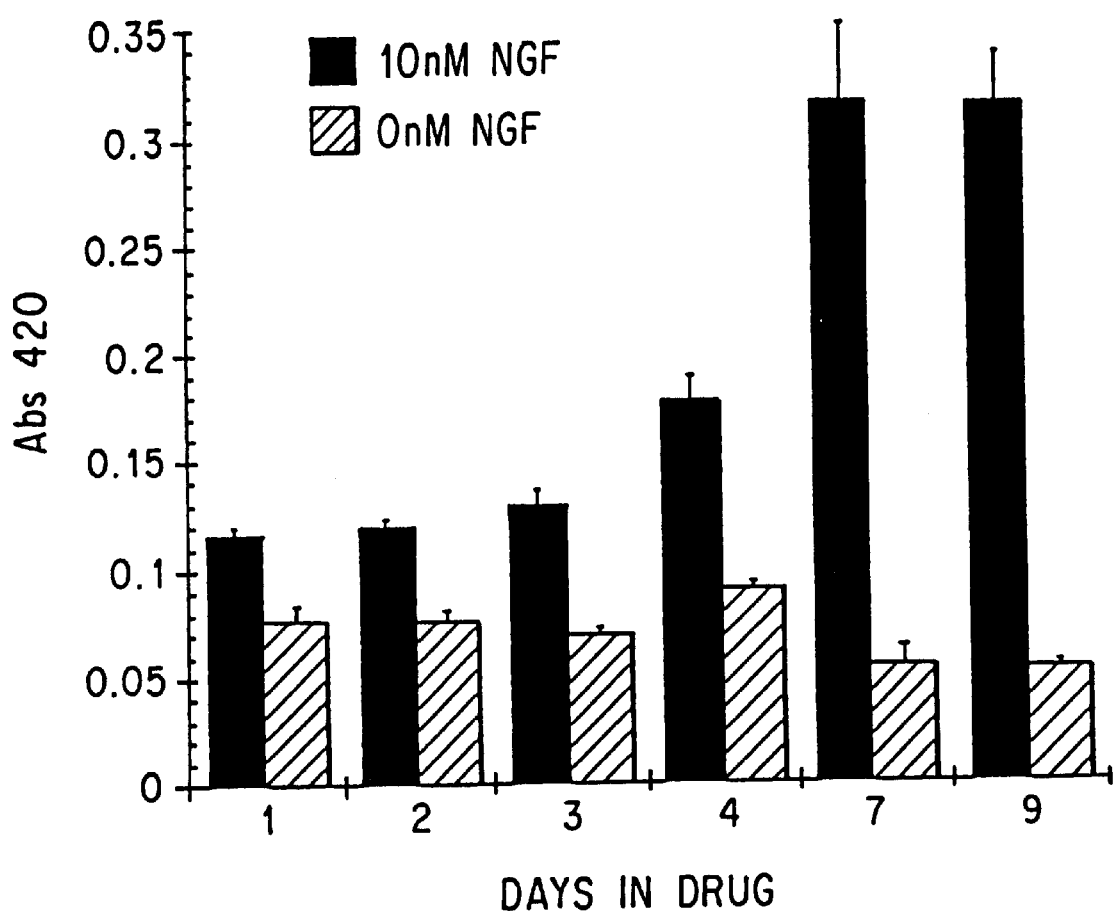
FIG. 3A illustrates the time-course of human nerve growth factor (NGF) stimulation of β-galactosidase activity in cells transfected with the human trk A receptor. Illustrated is a bar graph of the absorbance at 420 vs. days of incubation in the presence or absence of 10 nM NGF.

Nerve growth factor (NGF) is an agonist for the trk A receptor. NGF-stimulated trk A receptors activate tyrosine phosphorylation, and induce foci in NIH 3T3 cells. FIG. 3a illustrates data from an experiment where trk A receptor-transfected cells were grown in the presence or absence of NGF following the general procedure described above. A 10 cm plate of NIH 3T3 cells were transfected with 5 μg of trk A receptor DNA (cloned substantially as described by Kaplan et al., Science 252, 1991, p. 554, and Martin-Zanca et al., Mol. Cell. Biol. 9, 1989, p. 24) and 5 μg of β-gal DNA. The cells were washed after 24 hrs, and after 48 hrs the cells were transferred to 96 wells of a microtiter plate and grown in the presence or absence of NGF for the indicated number of days. β-gal activity was induced by NGF, with a marked induction observed within three days. The data shown in FIG. 3A were means of triplicate determinations (each from separate wells) +/− SD.

Figure 3B:
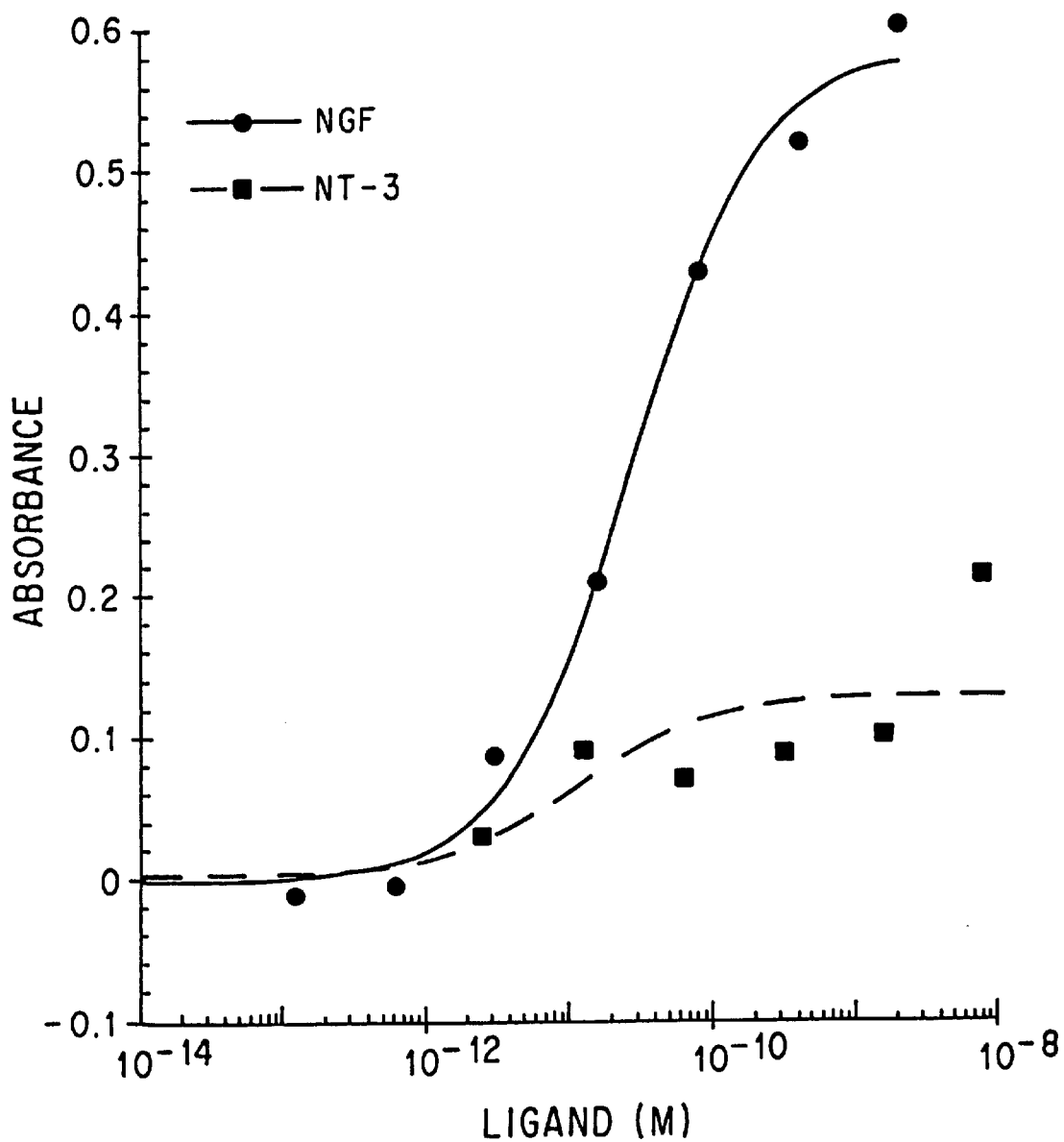
FIG. 3B illustrates the dose-response relationship of NGF and NT3 after three days of treatment.

FIG. 3B illustrates the NGF dose-response relationship for inducing β-gal after three days of NGF treatment. The NGF $ED_{50}$ of this response was similar to that observed of endogenous NGF receptor induced neurite outgrowth in PC 12 cells (Cordon-Cardo et al., Cell 66:173–183 (1991); Chao et al., Neuron 9:583–593 (1992)).

Also illustrated is the dose-response relationships of the related neutrotrophic factor NT3. Not shown is the fact that NGF was not able to induce amplification responses in cells transfected with the trk C receptor subtype, consistent with the known selectivity of neutrotrophin receptors (see also table 2).

Example 2
β-galactosidase Activity in Cells Transfected with Muscarinic Receptor Subtypes m1, m2, m3, m4 and m5

Muscarinic acetylcholine receptors that stimulate phospholipase c (m1, m3, m5) are able to stimulate cellular growth and induce foci in NIH 3T3 cells, only when the transfected receptors are activated by ligands that have agonist activity. In monoclonal lines isolated from NIH 3T3 cells transfected with these receptors, the agonist dose-response relationships for stimulation of phospholipase c, stimulation of mitogenesis and foci are identical, and these responses are blocked by the muscarinic receptor antagonist atropine. The m2 and m4 muscarinic receptors do not strongly stimulate phospholipase c in NIH 3T3 cells, nor do they induce foci. These data indicate that ligand-induced changes in cellular growth can be used as an assay of the pharmacology of some muscarinic receptor subtypes (Gutkind et al., PNAS 88, 4703 (1991); Stephens et al., Oncogene 8, 19–26 (1993)).

Figure 1A:
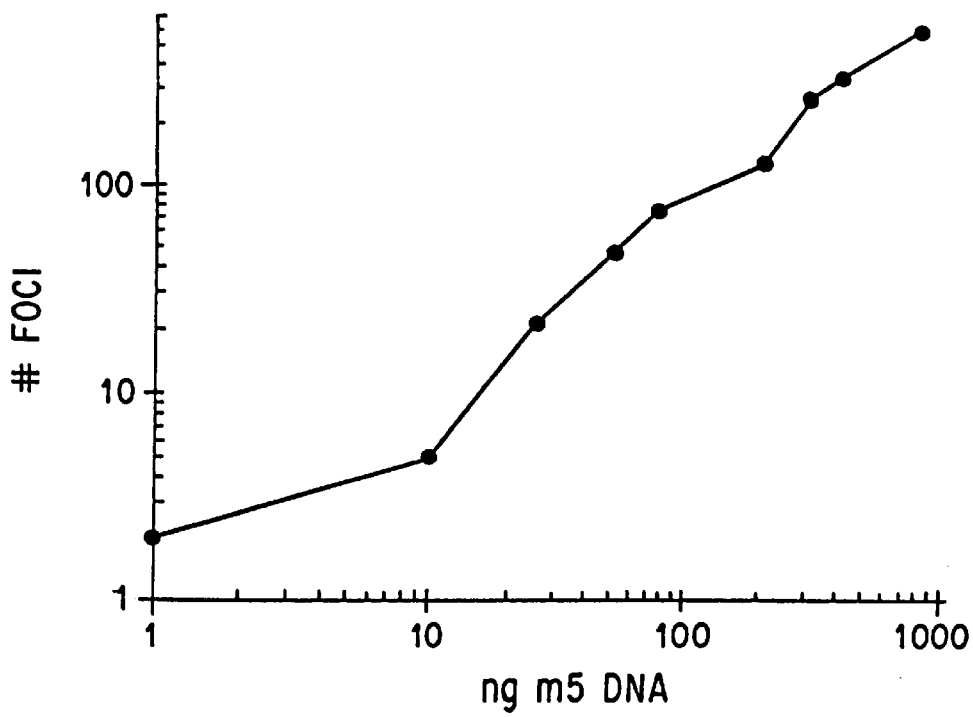
FIG. 1A is a plot of the number of foci vs. concentration of m5 DNA.

The dose-response relationship of m5 DNA for inducing foci in NIH 3T3 cells is illustrated in FIG. 1a. These data indicate that the focus response requires low concentrations of DNA (~1 ng) and is linear over a wide range of DNA concentrations (1 ng to at least 1000 ng). For 100 ng of m5

Figure 1B:
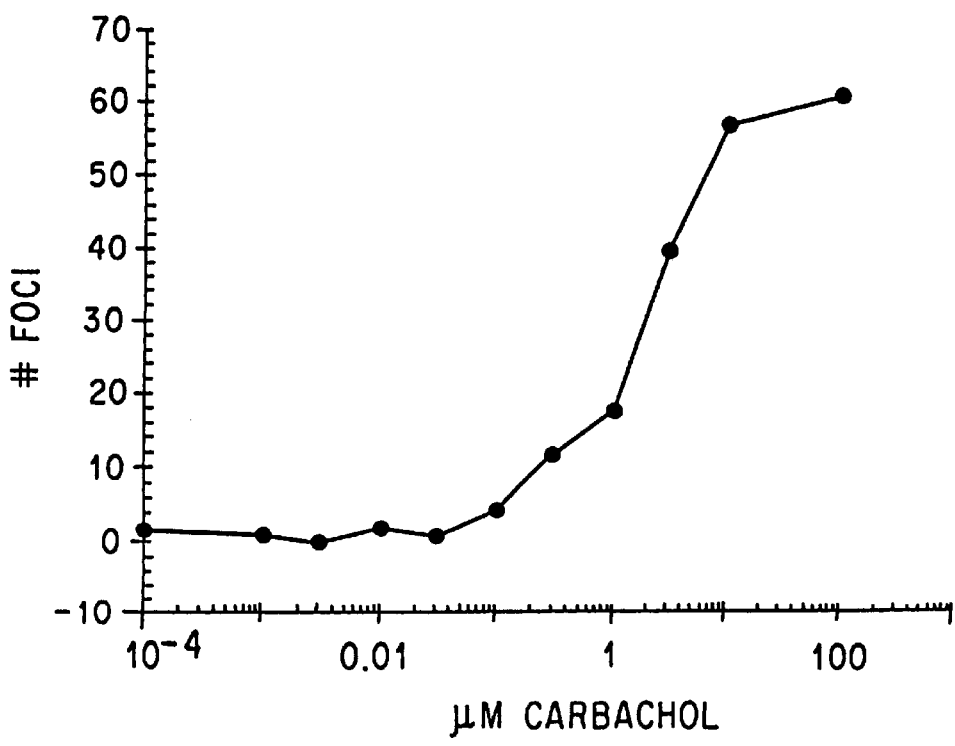
FIG. 1B is a plot of the number of foci vs. concentration of carbachol. Cells were stained and foci counted 2 weeks after carbachol treatment. Experiments were performed in 10 cm plates, and carbachol (100 µM) was applied 2 days after transfection, and was changed every 3–4 days.
Figure 2A:
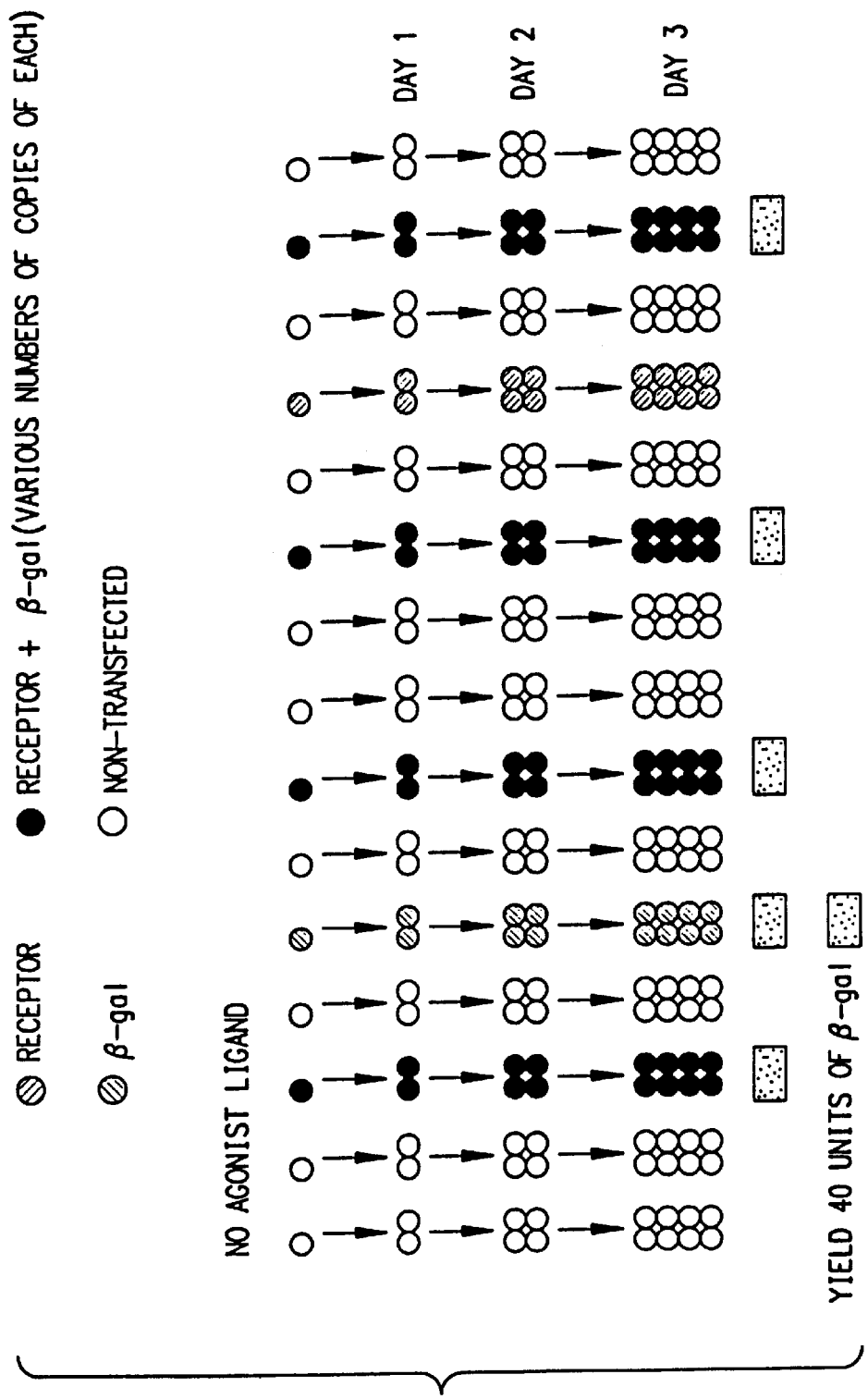
FIG. 2 is a schematic drawing of the Single Receptor Format, here agonist induction of receptor is detected as β-galactosidase activity. Receptor DNA and β-galactosidase DNA are co-transfected using a high concentration of both DNA's, conditions where the majority of cells that are successfully transfected will be transfected with both DNA's. Using the alcium phosphate precipitation procedure described below, only minority of cells in the culture will be transfected. In the illustrated example, cells divide once a day, and the presence of an agonist ligand doubles the rate of division (*) of cells transfected with the receptor.
Figure 2B:
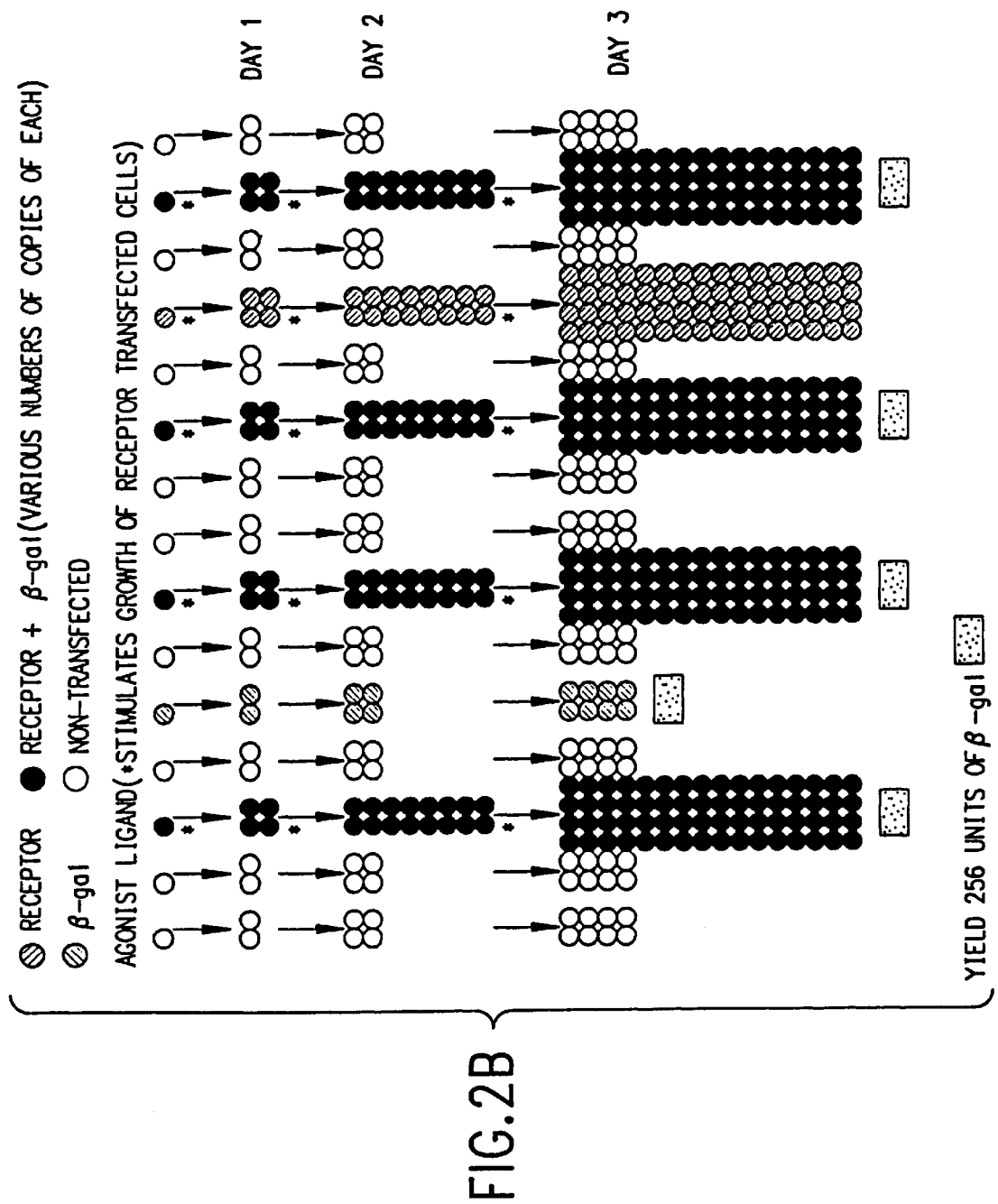

DNA, the dose-response relationship of carbachol for inducing foci is illustrated in figure 1b. Using the calcium phosphate precipitation conditions described above under the general protocol, a minority of cells in each culture are actually transfected with DNA. These data indicate that under conditions where low concentrations of DNA have been used to transfect a minority of cells within a culture, robust ligand-dependent responses are observed.

Muscarinic receptor subtypes, like many other receptors, are able to selectively interact with functionally distinct G-proteins. For example, m1, m3 and m5 receptors selectively stimulate phospholipase c by coupling with the G-protein Gq, and m2 and m4 selectively inhibit adenylyl cyclase by coupling with the G-protein Gi. m2 and m4 also selectively couple with the G-protein Go (Jones et al., in *Molecular Biology of G-protein-coupled receptors*, M Brann ed. Birhauser Boston. pp 170–197 (1992)). One strategy for altering the functional phenotype of a receptor is to express the receptor with a mutant G-protein. For example, if the receptor-coupling selectivity of Gq were changed to that of Gi, then m2 and m4 receptors would be able to activate such a mutant Gq. It has recently been shown that the carboxy-terminus of G-proteins directs their selectivity for different receptors. In our studies, we tested a chimera between Gq and the carboxy-terminal five amino acids of Gi (Gq-i5) or Go (Gq-i5 and Gq-o5 constructs are described in Conklin et al., *Nature* 363, 1993, p. 274).

Figure 4:
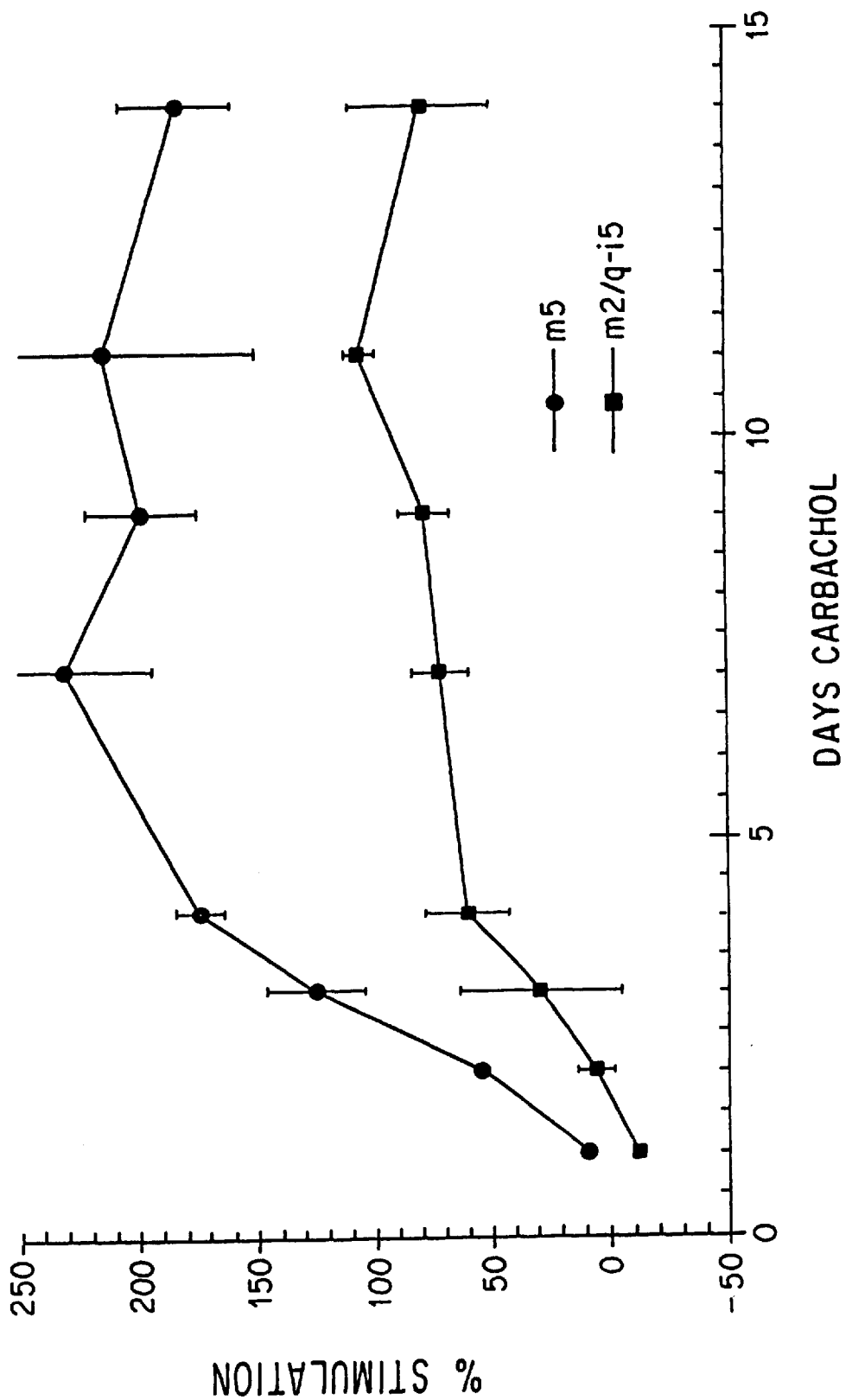
FIG. 4 illustrates the time-course of carbachol stimulation of β-galactosidase in cells tranfected with m5 and m2 muscarinic receptors.

The time-course of carbachol induction of β-galactosidase activity was investigated in NIH 3T3 cells (FIG. 4) transfected with m5 and m2 muscarinic receptors. Either 5 μg of human m5 muscarinic receptor DNA and 5 μg of a control plasmid DNA, or 5 μg of human m2 muscarinic receptor DNA and 5 μg of Gq-i5 DNA (m2/Gq-i5), were combined with 5 μg of β-galactosidase DNA to transfect 10 cm plates. After 48 hrs, the cells were transferred to wells of a 96 well plate for immediate treatment with carbachol. Carbachol treatment was continued for the indicated number of days, and media and carbachol were changed every three days.

In the case of the m2 receptor, the G-i5 chimera was co-expressed with with the receptor (5 μg of receptor and 5 μg of G-protein). In the absence of expressed G-protein, m2 receptors have no effect on β-galactosidase levels. For both the m2/q-i5 and m5 transfected cultures, carbachol was able to significantly induce β-galactosidase levels, and this effect reached a plateau at about five days of drug treatment. The abilities of Gq-i5 and Gq-o5 to mediate β-galactosidase responses were compared to stimulation of m4 receptors by carbachol. The ED50's of carbachol for m4/q-i5 was 0.037 +/− 0.046 and for m4/q-o5 was 0.032 +/− 0.047, and both combinations yielded similar maximal responses. These data indicate that m4 receptors couple with similar efficiencies to q-i5 and q-o5.

Based on the above time-courses and experiments where cell densities were optimized to yield maximal β-galactosidase signals, the general protocol for the Single Receptor Format described above was applied. The m1–m5 muscarinic receptors were cloned substantially as described by Bonner et al., *Science* 237, 1987, p. 527, and Bonner et al., *Neuron* 1, 1988, p. 403. For each of the m1, m3 and m5 muscarinic receptors, NIH 3T3 cells were transfected with 5 μg of receptor DNA and 5 μg of β-galactosidase DNA. For each of the m2 and m4 muscarinic receptors, NIH 3T3 cells were transfected with 5 μg of receptor DNA, 5 μg of Gq-i5 DNA, and 5 μg of β-galactosidase DNA. Data for the m1, m3 and m5 muscarinic receptors were collected 5 days after carbachol treatment, and data for the m2 and m4 muscarinic receptors were collected 4 days after carbachol treatment. No media changes were performed. Data were means from three-four independent wells, read directly from the original wells 4 hrs after addition of substrate and detergent. Lines are computer generated fits of the data to an equation for a single mass-action site of action.

Figure 6B:
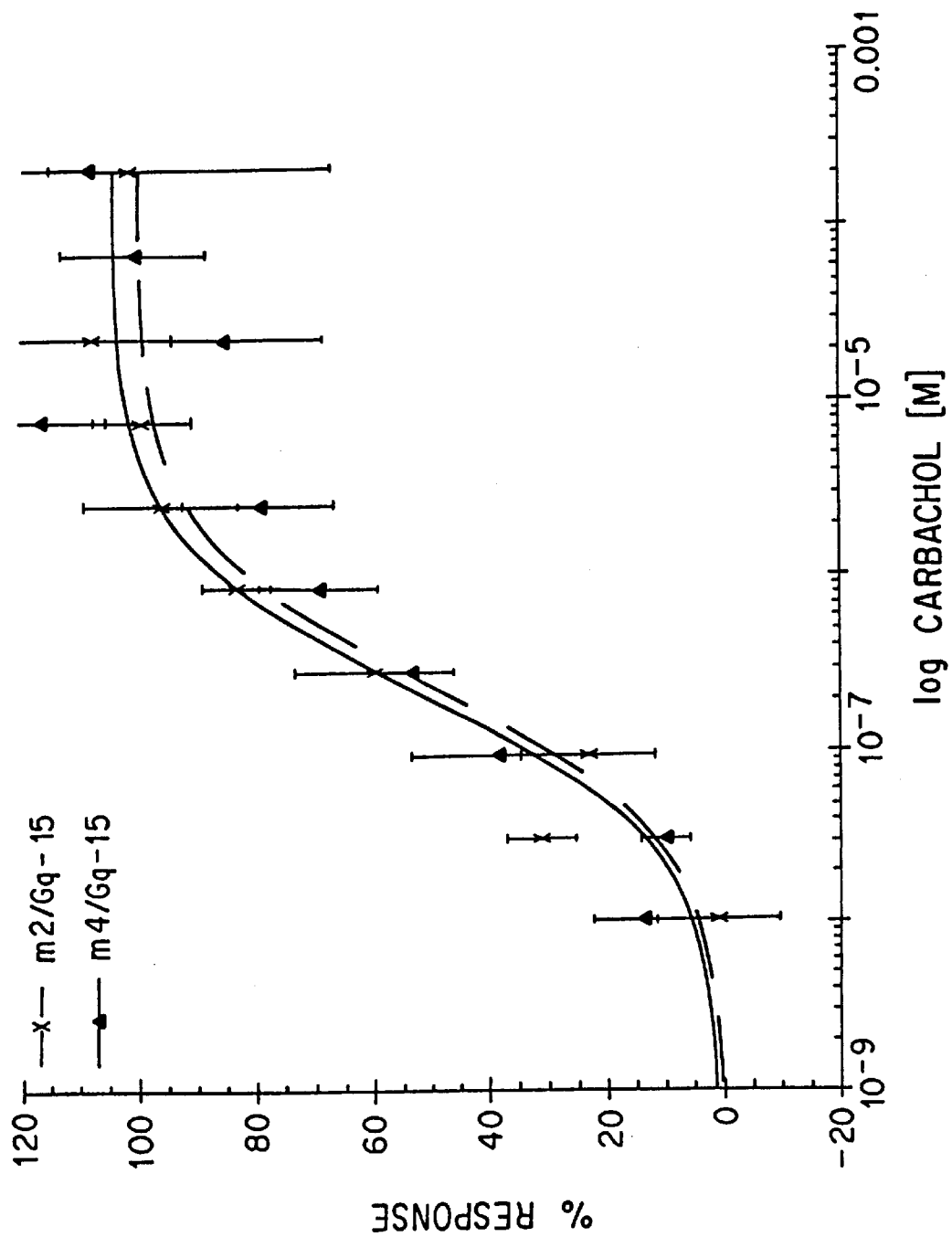
FIG. 6B illustrates the dose-response relationships of m2 and m4 muscarinic receptors.

The carbachol dose-response relationships of m1, m3 and m5 transfected cells was investigated (FIG. 6A). Similar experiments were performed with m2 and m4 receptors co-transfected with Gq-i5 (FIG. 6B). As illustrated, the general protocol permitted precise determinations of the $ED_{50}$'s of carbachol for these five receptors. These values are in good agreement with ealier measurements using foci induction (Gutkind et al., *Proc. Natl. Acad. Sci. USA* 88, 4703 (1991)), mitogenesis (Stephens et al. *Oncogene* 8:19–26 (1993)), second messenger and physiological responses (Jones et al. *Mol. Pharm.* 40:242–247 1991)). Also illustrated is a fit of the data to an equation for a single mass-action site of action. As indicated, all of the receptors obeyed this receptor mass-action relationship. Table 1 illustrates the pharmacologies of several muscarinic agonists and antagonists for the m1–m5 receptors evaluated using this assay. All of the antagonist data was in good agreement with parameters that have been previously evaluated using binding assays, with the exception that most antagonist have lower potency in these functional assays that in binding assays (reviewed in Jones et al. in *Molecular Biology of G-Protein Coupled Receptors*, op. cit.). Also, illustrated is the ability of the assay to discriminate between the responses of full and partial agonists. Partial agonist are often difficult to differentiate from full agonists in functional assays. Difficulties are often due to ceiling effects and receptor spareness. In fact, assays rarely combine a high sensitivity to weak partial agonists with an ability to discriminate full and partial agonists.

TABLE 1

Pharmacology of muscarinic acetylcholine receptors

| agonist | m1 | m2 | m3 | m4 | m5 |
|---|---|---|---|---|---|
| A. Pharmacology of Muscarinic Agonists - $EC_{50}$ [μM] (% Max) | | | | | |
| arecoline | 3.2 ± 0.7 | 0.025 ± 0.001 | 0.34 ± 0.11 | 0.13 ± 0.05 | 0.60 ± 0.05 |
|  | (86 ± 3) | (105 ± 0) | (66 ± 9) | (72 ± 3) | (77 ± 2) |
| carbachol | 6.5 ± 0.6 | 0.10 ± 0.04 | 1.4 ± 0.7 | 0.27 ± 0.07 | 0.11 ± 0.05 |
|  | (100) | (100) | (100) | (100) | (100) |
| McN A-434 | 1.1 ± 0.2 | 1.5 ± 0.6 | 2.2 ± 0.0 | 0.12 ± 0.02 | 1.0 ± 0.3 |
|  | (43 ± 2) | (108 ± 7) | (38 ± 2) | (84 ± 3) | (57 ± 4) |
| muscarine | 2.4 ± 0.8 | 0.06 ± 0.02 | 0.56 ± 0.25 | 0.32 ± 0.15 | 0.39 ± 0.18 |
|  | (84 ± 4) | (76 ± 1) | (84 ± 6) | (69 ± 2) | (86 ± 0) |

TABLE 1-continued

Pharmacology of muscarinic acetylcholine receptors

| agonist | m1 | m2 | m3 | m4 | m5 |
|---|---|---|---|---|---|
| oxotremorine | 0.39 ± 0.13 | 0.019 ± 0.010 | 0.21 ± 0.06 | 0.033 ± 0.014 | 0.055 ± 0.001 |
|  | (75 ± 10) | (100 ± 5) | (66 ± 5) | (102 ± 3) | (74 ± 2) |
| pilocarpine | 274 ± 30 | 25 ± 1 | 35 ± 3 | 60 ± 16 | 27 ± 10 |
|  | (79 ± 5) | (107 ± 4) | (54 ± 7) | (71 ± 8) | (71 ± 4) |
| B. Pharmacology of Muscarinic Antagonists -negative log $K_i$ [M] | | | | | |
| atropine | 9.0 ± 0.1 | 8.3 ± 0.3 | 8.9 ± 0.2 | 9.1 ± 0.0 | 9.1 ± 0.0 |
| pirenzepine | 7.7 ± 0.0 | 6.2 ± 0.0 | 6.6 ± 0.2 | 7.3 ± 0.2 | 6.9 ± 0.0 |
| 4-DAMP | 8.6 ± 0.0 | 7.6 ± 0.2 | 8.7 ± 0.3 | 9.1 ± 0.1 | 9.0 ± 0.2 |
| p-F-HHSiD | 6.6 ± 0.2 | 6.3 ± 0.1 | 7.5 ± 0.1 | 7.3 ± 0.1 | 7.1 ± 0.2 |
| methocrtramine | 6.3 ± 0.1 | 7.6 ± 0.1 | <6.0 | 6.4 ± 0.1 | <6.0 |

Dose-response relationships of muscarinic agonists and antagonists at the five cloned human muscarinic receptor subtypes. NIH 3T3 cells were co-transfected with a muscarinic receptor and β-galactosidase cDNAs. The m2 and m4 were also co-transfected with Gq-i5 cDNa. Amplification assays were performed using the Single Receptor Format. Data represent the mean (±SE) of 2–4 experiments.
A. Agonist Pharmacology. Individual $EC_{50}$ and maximal responses were derived by nonlinear regression of data from 8–10 concentrations of the indicated ligands, with 3–4 replicates per concentration. Maximum responses are indicated as a % of carbachol responses. Maximum responses for carbachol were defined using 200 μM (ml), 10 μM (m2, m4), 100 μM (m3) and 5 μM (m5).
B. Antagonist Pharmacology. Individual $IC_{50}$ values were derived by nonlinear regression of data from 8–10 concentration of the indicated ligands, with 3–4 replicates per concentration. $IC_{50}$ values were converted to Ki values using the Cheng-Prusoff equation. Antagonists were evaluated using carbachol at 50 μM (ml), 5 μM (m2, m4), 10 μM (m3) and 1 μM (m5).

Example 3
Luciferase Activity in Cells Transfected with the m5 and m2 (Gq-i5) Muscarinic Receptors Following the general protocol described above, amplification of the m5 muscarinic receptor and the m2 muscarinic receptor (co-transfection with Gq-i5) was determined using firefly luciferase (luc, pGL2-control vector, Promega) as a marker instead of β-galactosidase. Receptor, marker, and G-protein DNA concentrations were identical to those described for the β-galactosidase experiments in Example 2. The ED50's of carbachol were 0.22 +/− 0.1 μM for m5 and 0.14 +/0.11 μM for m2/q-i5 for inducing activity of firefly luciferase. Firefly luciferase was assayed as recommended by the manufacturer (Promega). The data obtained indicate that, like β-galactosidase, firefly luciferase can serve as a sensitive marker of muscarinic receptor activation by a ligand.

Example 4
Stimulation of Different Receptors

Receptors belonging to several functional categories have successfully been assayed using the the general protocol for the Single Receptor Format described above. The results are shown in Table 2 below. These data indicate that a wide range of receptors and related molecules can be assayed by our amplification assays. Illustrated are examples of receptors for a diversity of transmitters including monoamines, amino acids, peptides and large hormones (muscarinic receptors, Bonner et al., Science 237: 527, 1987; Bonner er al., Neuron 1: 403, 1988; dopamine D2 receptor, Stormann et al., mol. pharm. 37: 1, 1990; tachykinin receptor, Takeda et al., BBRC 179: 1232, 1991; Huang et al., BBRC 184: 966, 1992; Gerard et al., JBC 265: 20455, 1990; alpha 1 adrenergic receptors, Cottecchia et al., PNAS 85: 7159, 1988; Lomasney et al., JBC 266: 6365, 1991; alpha 2 adrenergic receptors, Regan et al., PNAS 85: 6301, 1988; Lomasney et al., PNAS 87: 5094, 1990; endothelin receptors, Arai et al., Nature 348: 730, 1990; Sakurai et al., Nature 348: 732, 1990; P53, Baker et al., Science 249: 912, 1990; G-protein mutants, Voyno-Yasenetskaya et al., JBC 269: 4721. A diversity of signal transduction classes are also illustrated: G-protein coupled receptors, tyrosine kinase linked receptors, G-proteins andoncogenes. In a few of these cases, focus assays have been used to assay ligand interaction with the illustrated receptors. In many cases, it has been shown that focus assays do not yield measurable responses (e.g., m2 and m4 muscarinic receptors with Gq-i5). A detailed analysis of pharmacology of alpha adrenergic receptors is also presented in Table 3.

TABLE 2

Receptors Assayed by Amplification

| Receptor | | Ligand $EC_{50}$ nM | | $R_{max}$ | Trans. Class |
|---|---|---|---|---|---|
| Adrenergic | phenylephrine | UK 14,304 | Epinephrine | | |
| alpha 1A | 460 ± 30 | | | +++ | Gq |
| alpha 1B | 110 ± 20 | | | +++ | Gq |
| alpha 2 C10 | | 200 | 430 | +++ | Gq/Gi |
| alpha 2 C2 | | 690 | 1,700 | +++ | Gq/Gi |
| alpha 2 C4 | | 780 | 50 | ++ | Gq/Gi |
| Dopamine | Quinpirole | | | | |

TABLE 2-continued

Receptors Assayed by Amplification

| Receptor | Ligand EC$_{50}$ nM | | | R$_{max}$ | Trans. Class |
|---|---|---|---|---|---|
| D2 | 0.5 ± 0.4 | | | ++ | Gi* |
| Endothelin | ET-1 | ET-2 | ET-3 | | |
| ET$_A$ | 0.079 ± 0.048 | 16 ± 4.1 | 2.1 ± 1.2 | +++ | Gq |
| ET$_B$ | 0.24 ± 0.2 | 17.6 ± 8.5 | 0.14 ± 0.07 | +++ | Gq |
| Glutamate | Quisqualate | | | | |
| metabatropic | 2,400 ± 1,400 | | | + | Gq |
| Insulin | Insulin | | | | |
| | 0.08 ± 0.08 | | | + | TK |
| Muscarinic | carbachol | oxotremorine | muscarine | | |
| m1 | 6,500 ± 600 | 390 ± 130 | 2,400 ± 800 | +++ | Gq |
| m2 | 100 ± 40 | 19 ± 10 | 60 ± 20 | ++ | Gi* |
| m3 | 1,400 ± 700 | 210 ± 60 | 560 ± 250 | +++ | Gq |
| m4 | 270 ± 70 | 33 ± 14 | 320 ± 150 | ++ | Gi* |
| m5 | 110 ± 50 | 55 ± 1 | 390 ± 180 | +++ | Gq |
| Neurotrophin | NGF | NT3 | | | |
| trk A | 1.2 ± 0.6 ng/ml | >1000 ng/ml | | ++++ | TK |
| trk C | | 2.4 ± ng/ml | | ++++ | TK |
| Prostanoid | Fluprostenol | MB28767 | | | |
| FP | 2 ± 1 | | | +++ | Gq |
| EP3 | | 270 ± 190 | | ++ | Gi |
| Tachykinin | substance P | neurokinin A | neurokinin B | | |
| NK1 | 7 ± 3 | 14 ± 5 | 99 ± 50 | +++ | TK |
| NK2 | 65 ± 6.5 | 21 ± 6 | 1.3 ± 0.7 | +++ | TK |
| NK3 | 164 ± 59 | 11 ± 2 | 100 ± 20 | +++ | TK |
| Mutant/ | | | | | |
| Activated | | | | | |
| v-ras | | | | ++++ | |
| p53-H175 | | | | +++ | |
| p53-W248 | | | | +++ | |
| G-12-229L | | | | +++ | |
| G-q-183C | | | | ++ | |
| m5-164 | | | | +++ | Gq |
| G-protein | | | | | |
| G-q | | | | +++ | |
| G-12 | | | | +++ | |

Receptors and other proteins that induce amplification responses in NIH 3T3 cells. All clones were tested using the single receptor format. Ligands were tested using 7–9 doses in triplicate. R$_{max}$ indicates the maximum response that was observed with each clone in arbitrary units relative to the other clones (++++ highest, + lowest). The known signal transduction classes of receptors are indicated (TK = tyrosine kinase). Some receptors (*) required the coexpression of the G-protein Gq-i5 to mediate a response. In the case of the mutant-activated clones (oncogenes in some cases), the indicated amino acid substitutions caused the proteins to induce significant amplification responses in the absence of added ligand. For the indicated wild-type G-proteins, the G-proteins could be assayed when co-expressed with a receptor (R). G-proteins are named by the nomenclature of Conklin et al. (Nature 363:274–276, 1993). M5 refers to the constitutively active m5 receptor described in FIG. 13.

TABLE 3

Agonist Pharmacology of α2 Adrenergic Receptors - EC$_{50}$ nM/Max Response

| Agonist | α2-C2 | α2-C4 | α2-C10 |
|---|---|---|---|
| Epinephrine | 1,700/++ | 50/+ | 430/++ |
| Norepinephrine | 7,200/++ | 2/+ | – |
| Clonidine | ± | >10,000/++ | – |
| p-I-Clonidine | 50/+ | – | – |
| p-NH2-Clonidine | 400/+ | ± | ± |
| BHT 920 | >10,000/++++ | >10,000/++++ | >10,000/++++ |
| BHT 933 | >10,000/++++ | ND | >10,000/++ |
| Guanfacine | 2,500/++++ | ± | 4,600/++ |
| Prazocin | 8,700/++ | >10,000/++ | ± |
| Oxymetazoline | 220/++++ | >10,000/+ | 4,600/++ |
| Rilmenidine | ± | 480/+ | ± |
| Dexmedetomidine | 2/+++ | ± | ± |
| Moxonidine | 1,500/++ | 2,000/+ | 4,400/++++ |
| Isoproterenol | ± | >10,000/+ | – |
| UK 14,304 | 690/++ | 780/+ | 200/+++ |

Agonist Pharmacology of cloned alpha2 adrenergic receptors. Dose-response relationships of adrenergic agonists at three cloned human alpha 2 adrenergic receptor subtypes. NIH 3T3 cells were co-transfected with adrenergic receptor and β-galactosidase cDNAs. Amplification assays were performed using the single receptor format. Data represent the mean of 203 experiments. Individual EC$_{50}$ and maximal responses were derived by nonlinear regression of data from 8–10 concentrations of the indicated ligands, with 3–4 replicates per concentration.

Maximum responses are indicated relative to other ligands at a given receptor (++++ highest, + lowest). Overall the C2 and C10 mediated more robust responses than C4.

(ND) not determined, (±) a very small response was observed, but reliable values could not be calculated.

Example 5
Random Mutagenesis of the m5 Muscarinic Receptor

Figure 7:
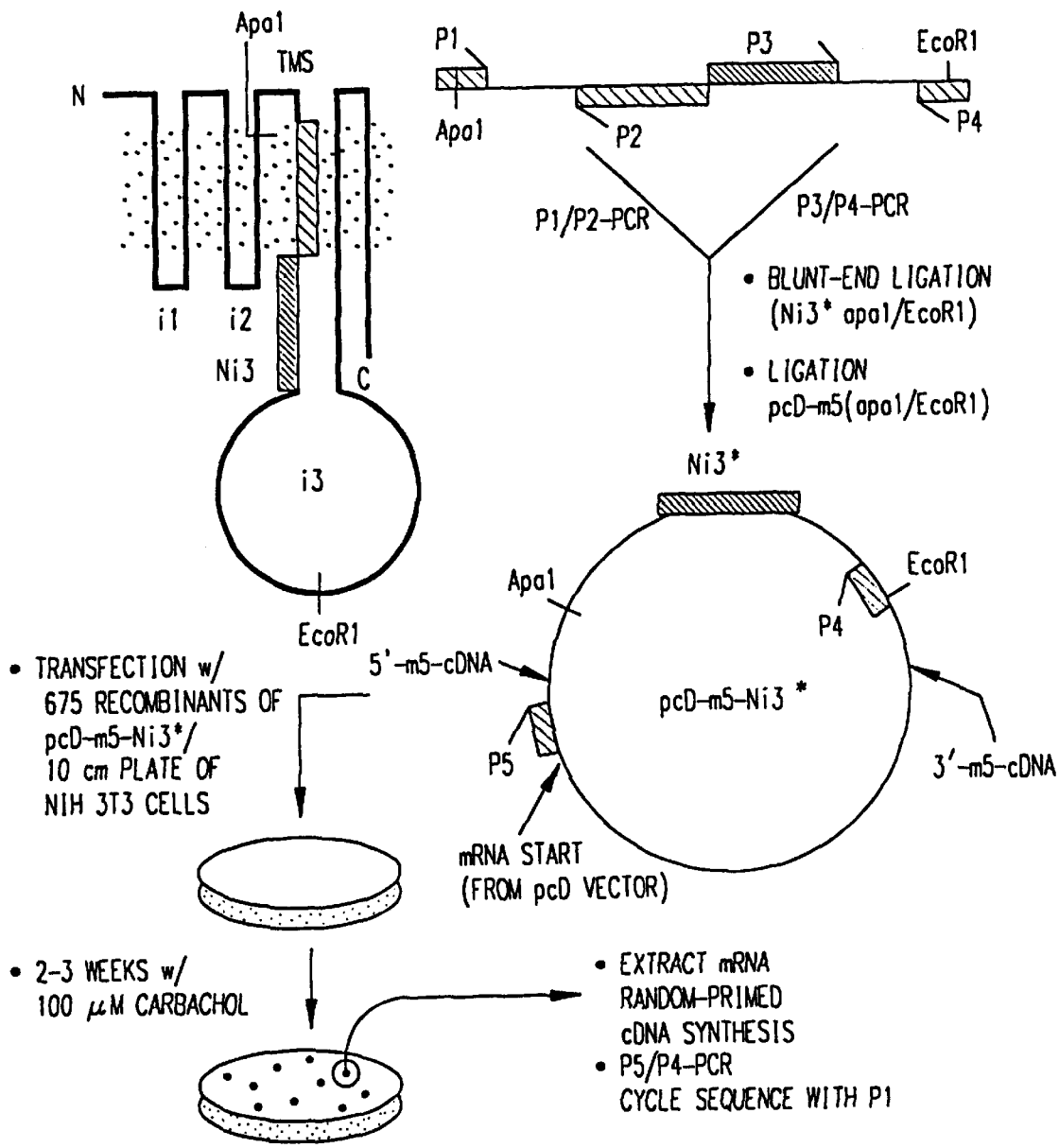
FIG. 7 is a schematic drawing showing a strategy for random-saturation mutagenesis of the m5 muscarinic acetylcholine receptor (SEQ ID NO:1).

To illustrate the utility of the Multiple Receptor Format, the m5 receptor was subjected to random mutagenesis over the N-terminal 20 amino acids of the third intracellular loop (N-i3), adjacent to the fifth transmembrane domain (TM5), region of the receptor that is involved in coupling to G-proteins. Two PCR products were prepared such that the reverse primer (P2) for the first product comprised the entire TM5 domain and the forward primer (P3) for the second product comprised the entire N-i3 domain To incorporate mutations, an equimolar mixture of the four bases were substituted at a 15% rate for wild-type nucleotides during synthesis of the P3 primer. The outer primers (P1 and P4) contain Apa1 and EcoR1 restriction sites for subsequent cloning. The two PCR products were treated with T4 DNA polymerase to create blunt ends, ligated to yield concatamers, and restricted with Apa1 and EcoR1 to release the randomly-mutated (*) Ni3*Apa1/EcoR1 inserts. Inserts were ligated into a Apa1/EcoR1 fragment of the pcD-m5 yielding a population of mutant m5 receptor cDNA (pcD-m5-Ni3*). The overall cloning strategy is shown in FIG. 7. A cDNA library of receptors, each with a different set of random mutations, was used to transfect NIH 3T3 cells. Transfections were performed with 450 ng of library cDNA (675 recombinants) per 10 cm plate. The NIH 3T3 cells were grown in the presence of 100 $\mu$M carbachol until foci were formed. After 2–3 weeks, macroscopically visible foci are removed from the plate, total RNA was extracted, and cDNA synthesized using random-hexamers as primers. These cDNA templates were used to amplify 1.6 kb fragments using P4 and P5 as PCR primers. P5 is complementary to a plasmid DNA sequence that is transcribed but is upstream of the m5 receptor cDNA. Thus, endogenous genomic sequences could not be amplified. The PCR products were directly sequenced using Taq polymerase in a cycle-sequencing rotocol using P1 as a primer.

Figure 9:
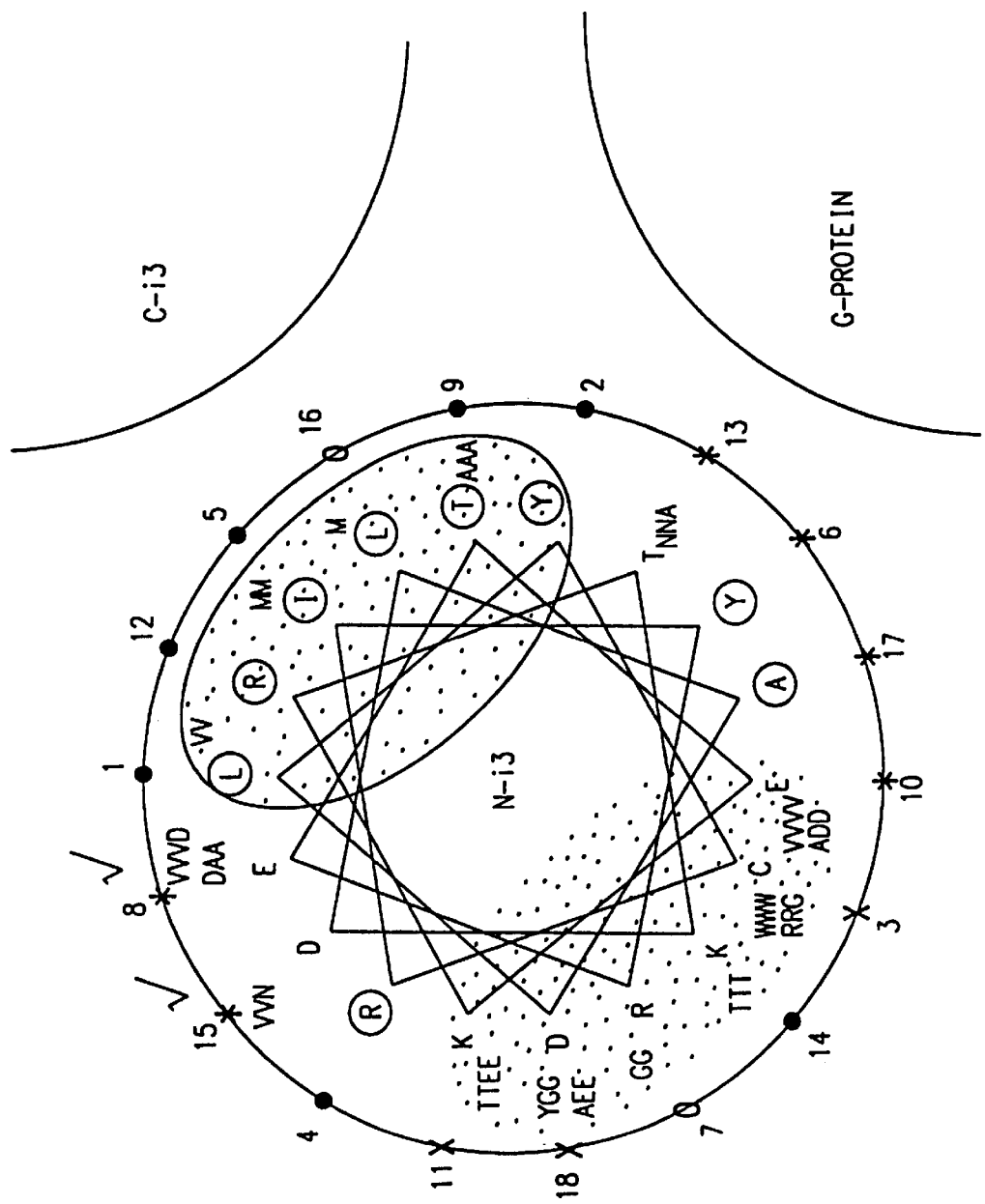
FIG. 9 is a schematic drawing showing a helical representation of the mutated domain of the m5 muscarinic receptor (SEQ ID NO:12). The domain is viewed from the intracellular space. C-i3 represents the C-terminal region of the i3 loop. Amino acid substitutions (from FIG. 8) are indicated by small letters. Positions where only conserved substitutions were isolated are circled. The large outlined and shaded oval encompasses the amino acid positions in which only conserved substitutions were observed. This is predicted to be the functionally critical face of the helix. The large shaded oval encompasses amino acids positions where nonconserved substitutions were observed at every position. This is predicted to be a functionally noncritical face of the helix. The large outer circle indicates the numbering of the amino acids starting at TM5. Classification of the amino acids with respect to homologies with the other muscarinic receptors are indicated on this circle using symbols that are defined in FIG. 8. Checks indicate positions in the m1 muscarinic receptor that tolerate radical substitutions as judged by site-directed mutagenesis.
Figure 10:
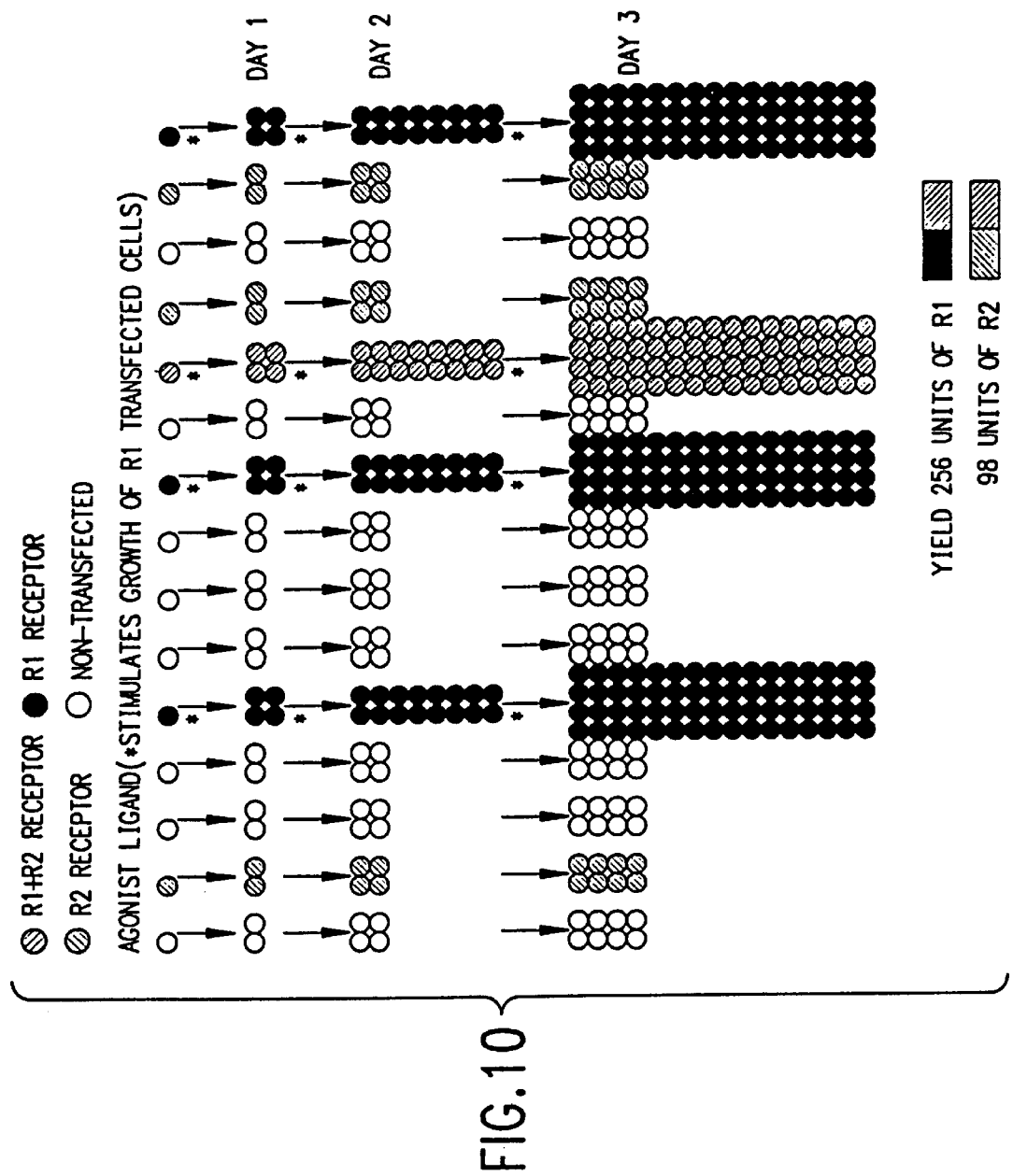
FIG. 10 is a schematic drawing of an example of the Multiple Receptor Format. In this example, a low concentration of two receptor DNA's (R1 and R2) are used for transfection. Under these conditions, very few of the cells will be simultaneously transfected with R1 and R2. Thus a R1 ligand will selectively amplify R1-expressing cells.

As illustrated in FIGS. 8 and 9, many different mutant receptors were identified in foci. These data allowed predictions concerning the likely structure of the region of the muscarinic receptor that is involved in G-protein-coupling. On a technical level these data indicate that when modest concentrations of receptor DNA are used, a single plasmid DNA is able to tranfect a NIH 3T3 cell and allow the ligand carbachol to stimulate growth of the cell resulting in a foci, and that the mutant receptor that induced the foci could be identified by DNA amplification procedures.

Figure 5:
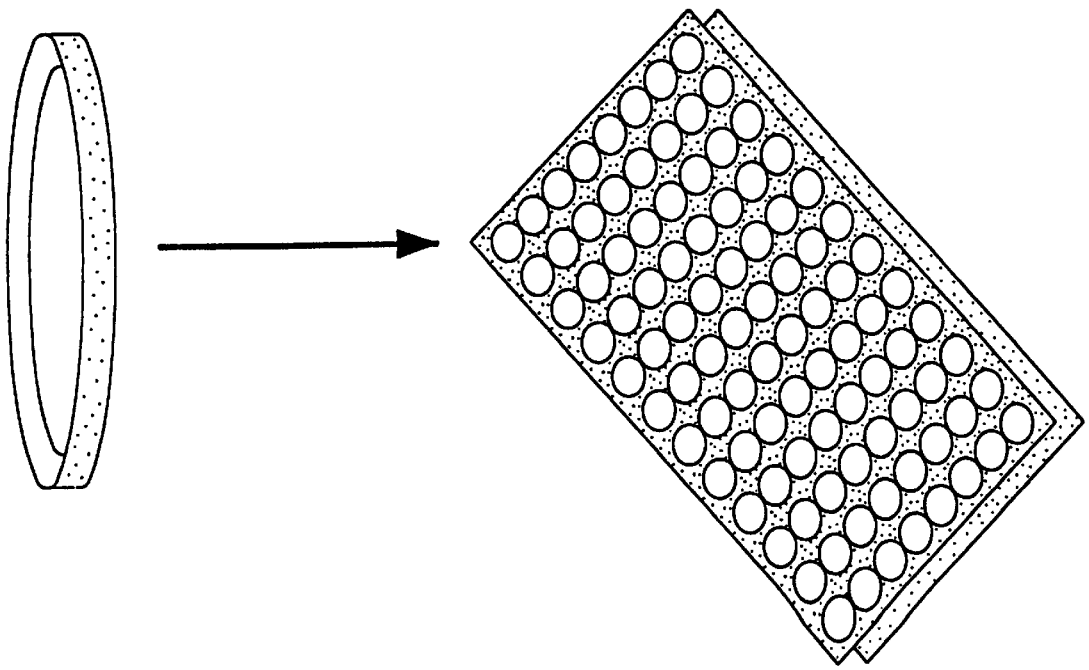
FIG. 5 is a schematic drawing showing an example protocol that can be used to assay receptors in a Single Receptor Format.
Figures 13A, 13B:
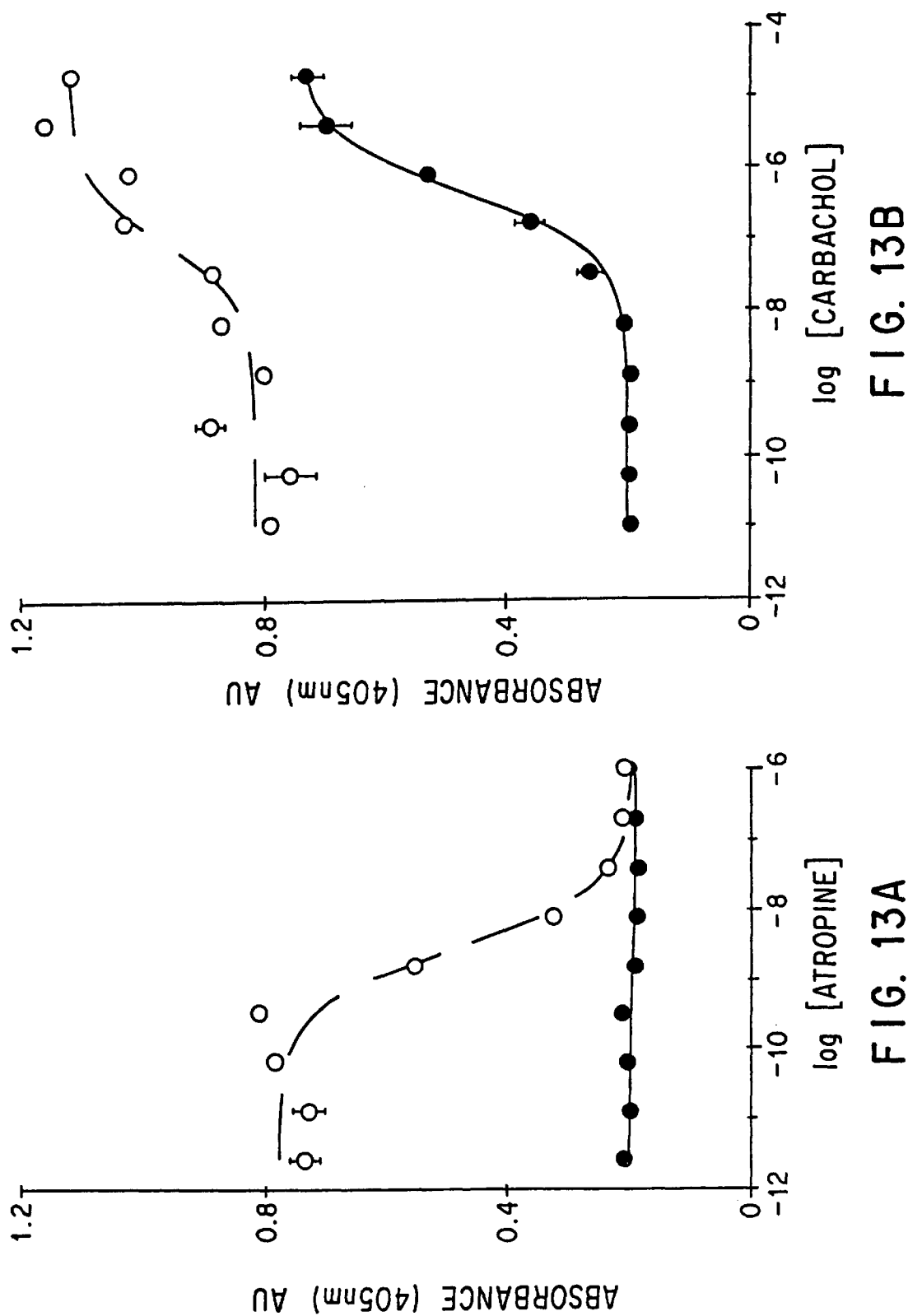
FIG. 13 illustrates the agonist and antagonist phenotypes of a mutant m5 receptor. Ten cm plates of NIH 3T3 cells were transfected with 1.5 µg of wild-type m5 (•) or m5-160 mutant receptor (o), and 3 µg of β-gal cDNA. Assays were performed as described in FIG. 5 after incubation in the indicated ligands for four days.
Figure 14:
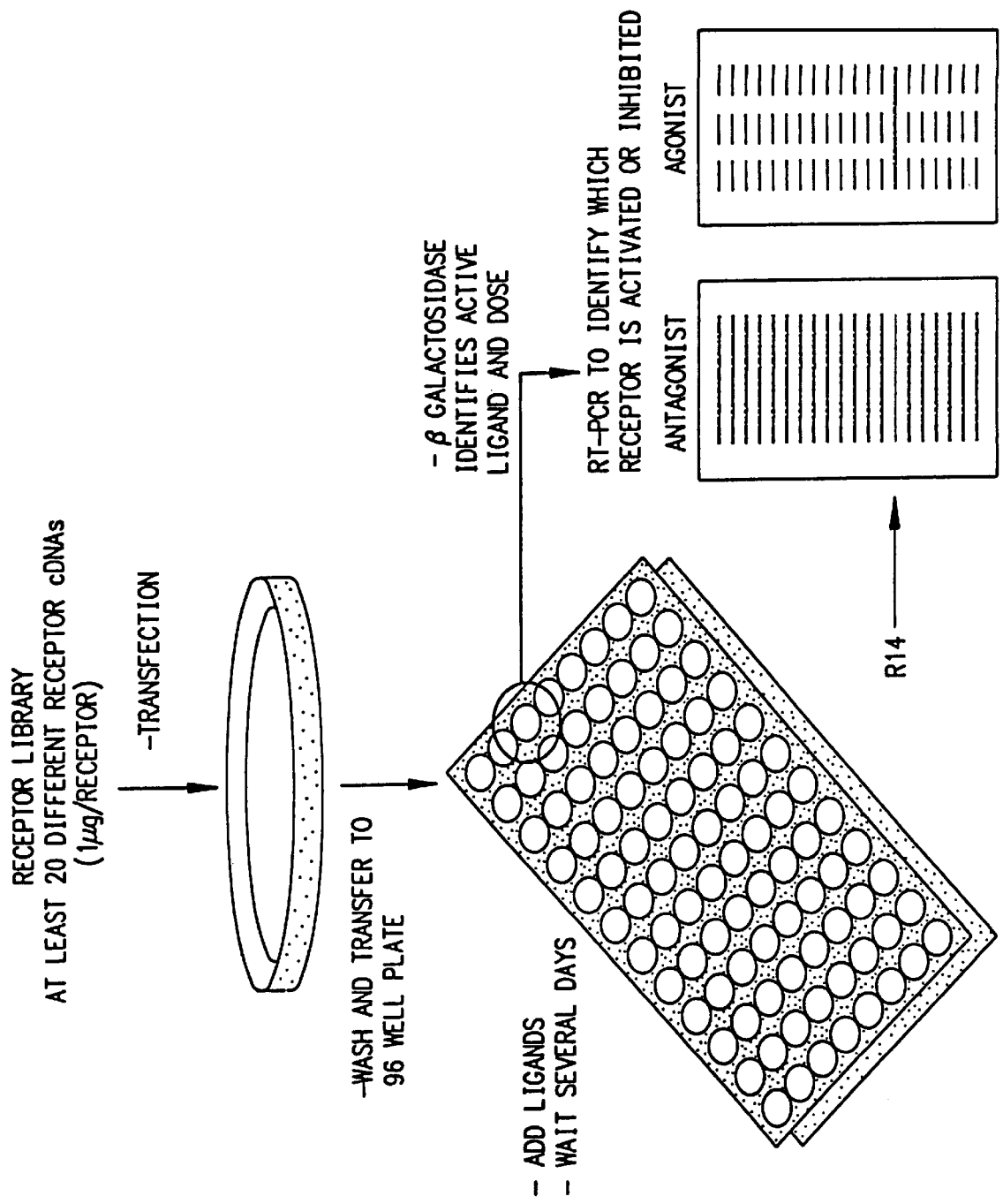
FIG. 14 is a schematic drawing of an embodiment of the Multiple Receptor Format where several receptors are assayed simultaneously using a combination of β-galactosidase and DNA amplification assays.

Example 6
Random Mutagenesis of the m5 Muscarinic Receptor Assayed by Amplification of Beta-galactosidase Using random mutagenesis strategies analogous to that described in FIG. 7, we have introduced mutations into regions of the m5 receptor thought to be involved in ligand binding and G-protein coupling. To assay these mutants a small scale plasmid preparation is made for each clone. This is performed using mini Qiagen anion exchange columns. These DNA preparations are used in transfections and assays in modifications of the Single Receptor Format. Modifications involve a proportional scale down in NIH 3T3 cell numbers and DNA amounts from those used for 10 cm plates, to amounts appropriate for individual wells of 6 well or 24 well plates. In the case of transfections performed in 24 well plates, beta-gal assays are performed directly in the wells used for transfection without an intermediate transfer step (e.g., the 10 cm plate to 96 well plate transfer of the standard Single Receptor Format, FIG. 5). Using these procedures we have screened several hundred clones for a variety of functional phenotypes. To identify mutant receptors that retain the ability to respond to agonist, we screen with high concentrations of agonist. To identify mutants that have elevated activity in the absence of ligand, we screen mutants in the absence of agonist and/or in the presence of antagonist. One clone that was isolated by this procedure is illustrated in FIG. 13. Relative to wild-type, this clone has a significantly elevated response in the absence of ligand, and this basal response is blocked by antagonists. These data indicate the utility of amplification assays for the identification of receptors with mutant phenotypes.

Example 7
Multiplex Receptor Format

Figure 11:
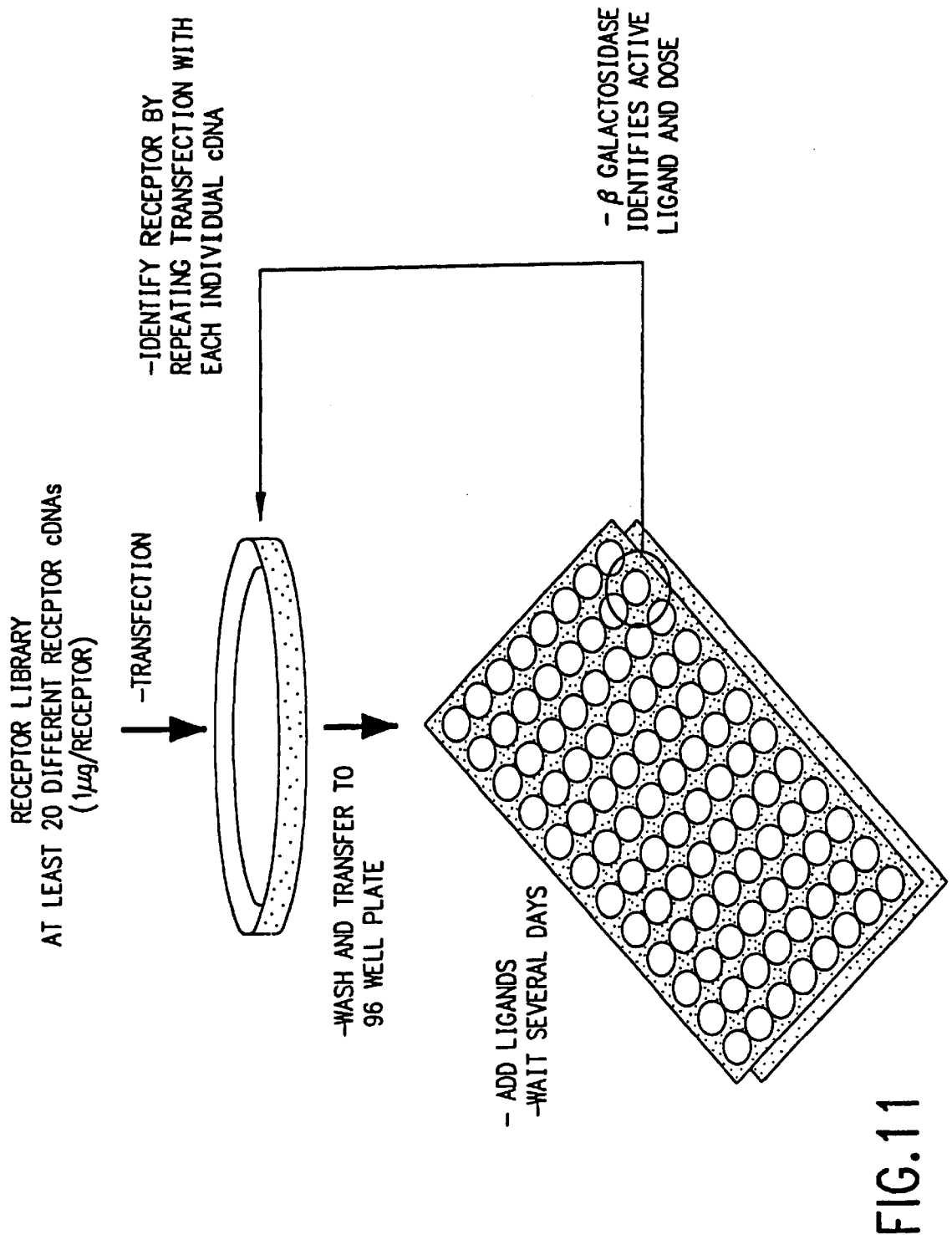
FIG. 11 is a schematic drawing of an embodiment of the Multiple Receptor Format where several receptors are assayed simultaneously using only β-gal assays.
Figure 15A:
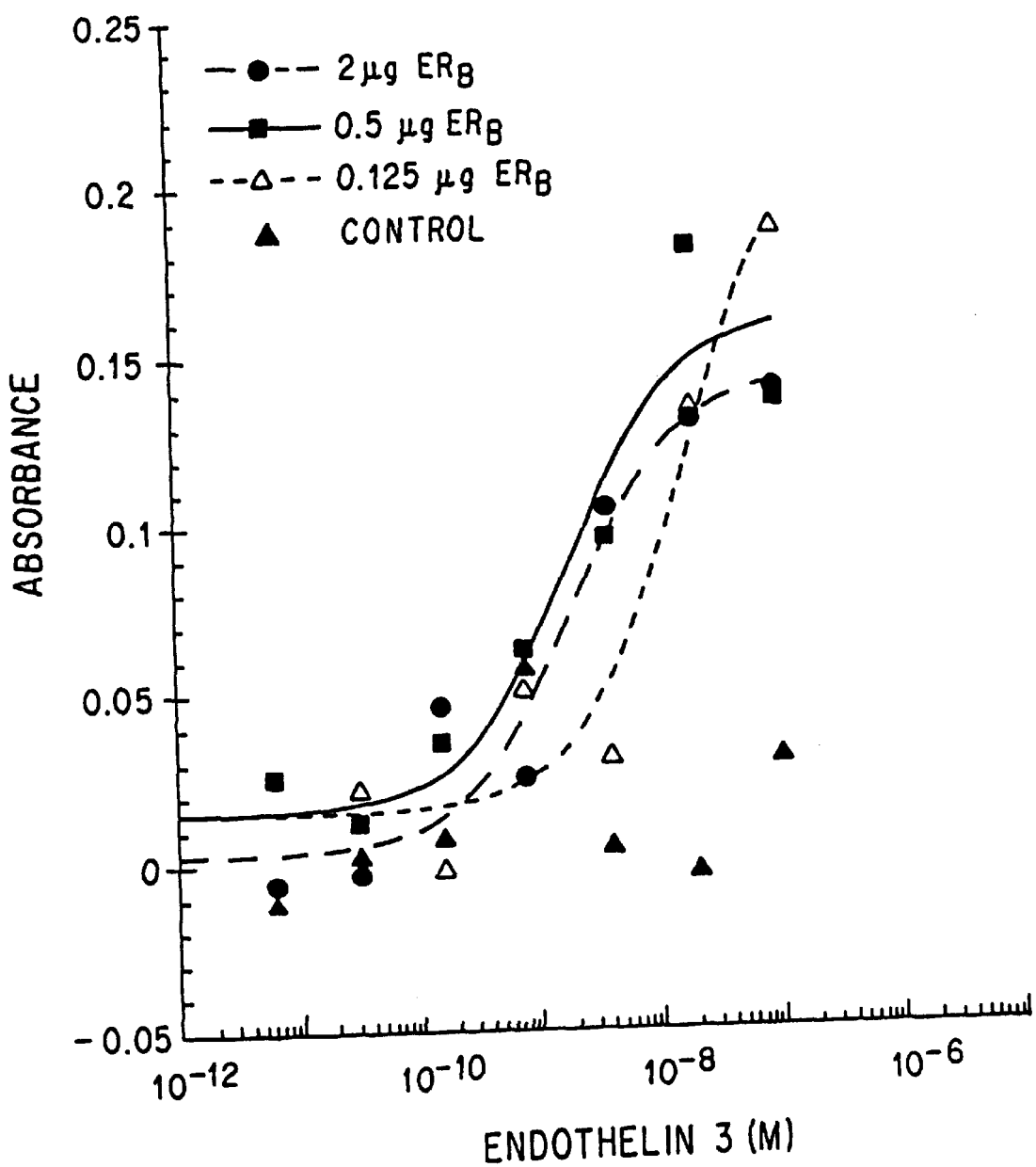
FIG. 15 illustrates the ligand and receptor cDNA dose/response relationships of the FP prostanoid and $ER_B$ endothelin receptors. Ten cm plates of NIH 3T3 cells were transfected with the indicated concentrations of receptor cDNA. Cells were incubated in wells of a 96 well plate for 4 days with the indicated concentration of ligands. All of the transfections also contained 2.5 μg of the D2 receptor and 2.5 μg of the β-gal cDNAs.
Figure 15B:
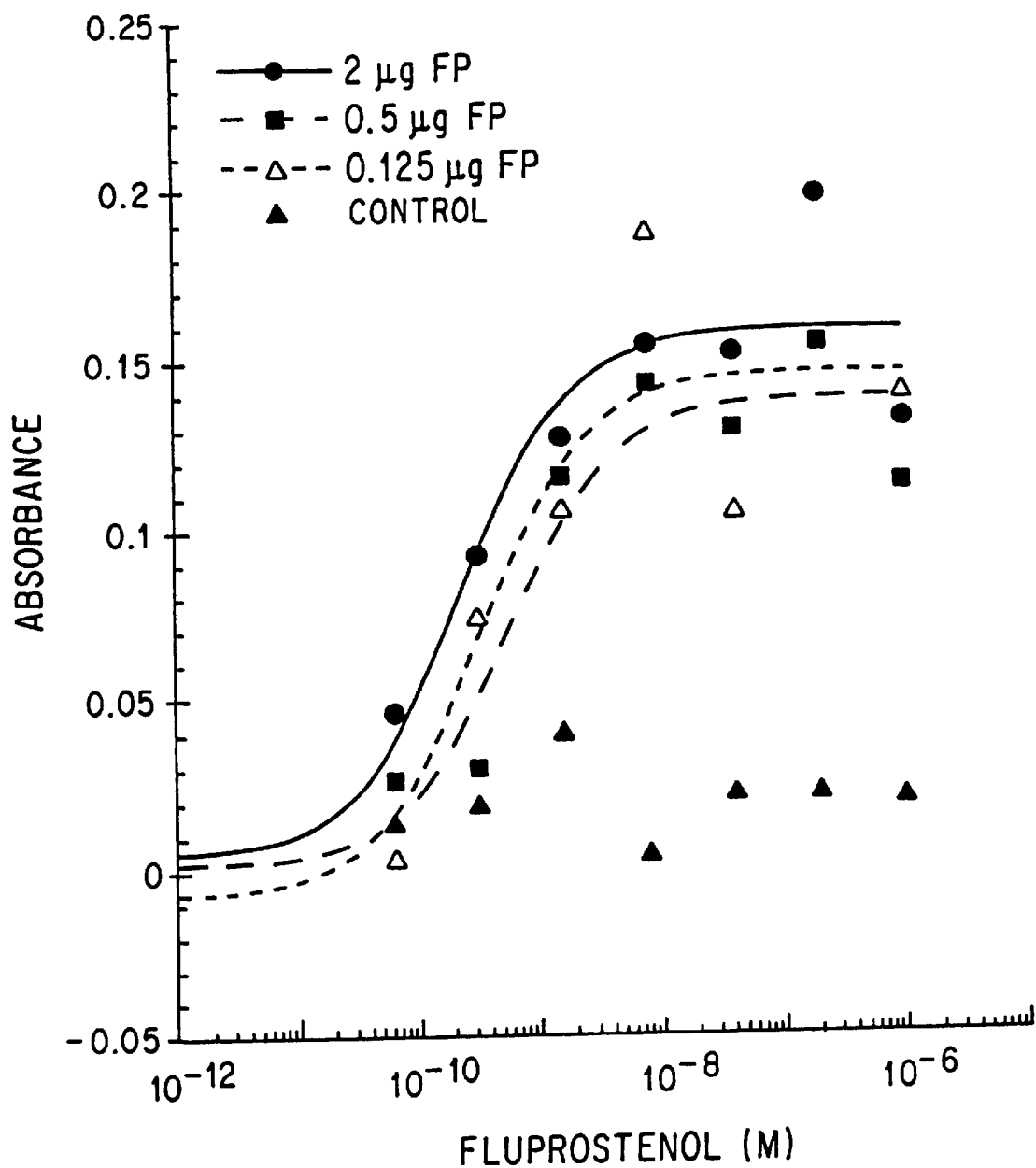
Figure 16:
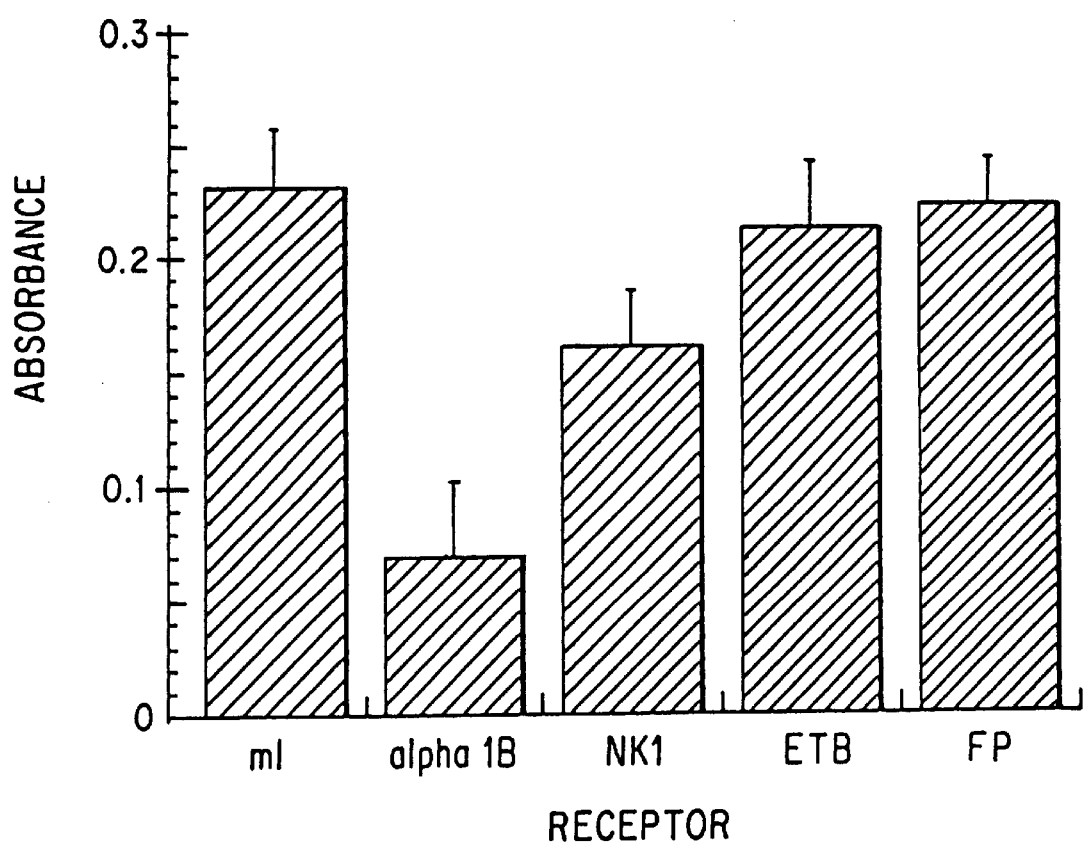
FIG. 16 illustrates the maximal ligand-induced responses of the indicated receptors, as assayed using cotransfected cultures using a Multiple Receptor Format similar to that described in FIG. 11. Ten cm plates of NIH 3T3 cells were transfected with 0.5 μg of each of the five test DNAs, 2.5 μg of D2 receptor cDNA, and 2.5 μg of 6-gal cDNA. Seven doses of agonist ligands selective for each of the receptors were tested (m1/carbachol: alpha 1B/phenylephrine. NK1/substance P: ETB/endothelin-3: FP/fluprostenol). Cells were incubated in wells of a 96 well plate for 4 days with each ligand. Maximal responses were calculated by fitting the data to a model of a single mass-action site. Separate experiments demonstrated that each of these ligands were unable to induce responses in the absence of its indicated target receptor.

One configuration of the Multiplex Receptor Format is illustrated in FIG. 11. In this example, several receptors cDNAs are cotransfected with beta-gal cDNA into a culture of NIH 3T3 cells. After addition of ligands an effective ligand/receptor interaction is identified by a positive beta-gal response. Data supporting the feasibility of this approach is illustrated in FIG. 15. In these examples, no signal is lost when endothelin and prostenoid receptor DNA is substantially reduced in concentration. Empirical data using multiple receptors is illustrated in FIG. 16. In this example, ligand responses to muscarinic, adrenergic, neurokinin, endothelin and prostenoid receptor activation were assayed in cotransfected cultures. In this experiment an excess of inactive receptor DNA was used to simulate a 10 fold multiplexed assay (10 receptors assayed simultaneously).

Example 8
Disease Gene Assay and Identification

Figure 12:
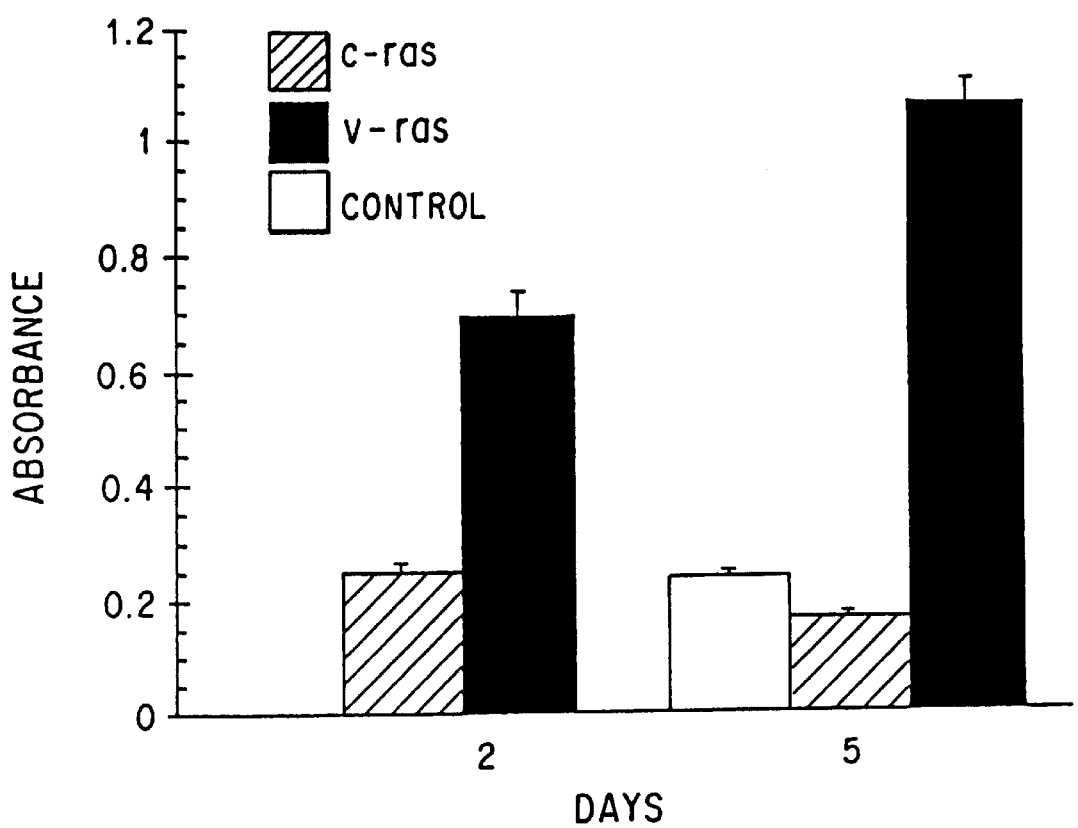
FIG. 12 illustrates the responses of cells to the oncogene V-ras. Six well plates of NIH 3T3 cells were transfected with 1 µg of V-ras or n-ras and 1 µg of 6-gal cDNA. Assays were performed using the Standard Single Receptor format as described in FIG. 5. Controls were performed using m5 receptor transfected cells without an activating ligand.

Many diseases are caused by mutations in receptors and/or associated signal transducing proteins. The best characterized examples are the oncogenes, but other examples include genes associated with retinitis pigmentosa, color blindness and insulin dependent or independent diabetes. Other examples will be well known to those skilled in the art. Among the best characterized oncogenes are mutant forms of the small G-protein ras. As illustrated in FIG. 12, mutant ras (v-ras), but not wild-rype ras (c-ras), is able to mediate significant responses in amplification assays. As summarized in Table 2, other oncogenes such as mutant forms of p53 and the G-protein G12 are able to mediate amplification responses. Also as noted in Example 6, a mutant form of the m5 receptor that is active in the absence of agonist was identified by amplification assays. Together these data indicate that amplification assays is a powerful approach to both the assay and idenfication of disease genes. The procedure for disease gene identification is as follows. 1) The coding region of a receptor suspected in a given disease is amplified by PCR. Amplifications can be performed using individuals or populations of individuals with disease. 2) The receptor is tested by amplification assays for activity in the absence of ligand, and/or inappropriate ligand sensitivity. By "inappropriate ligand sensitivity" is meant that a mutant form can be expected to respond to ligand at a lower concentration than the wild-type form. In addition, mutant forms' elevated activity will also be blocked by antagonist as shown, for example, in FIG. 13. Assays can be performed one at a time as in Example 6, or several patient DNAs could be tested simultaneously using the Multiplexed assays described in Example 7.

Example 9
Assay of Chimeric Receptors

Figure 17:
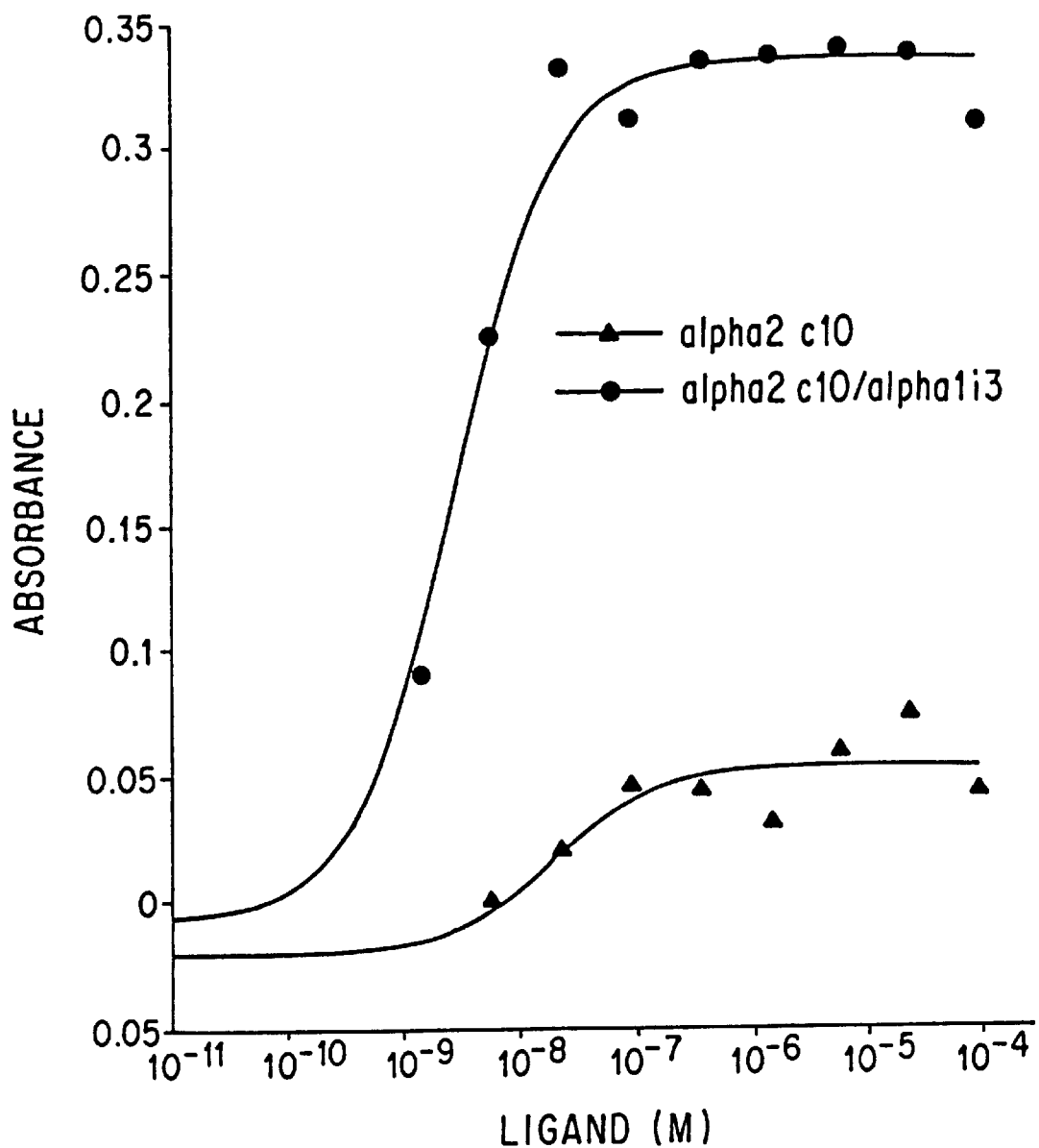
FIG. 17 illustrates the dose-response of wild-type and chimeric alpha 2 adrenergic receptors for the agonist UK 14,304. The indicated doses of agonist were assayed using the Single Receptor Format. Five μg of receptor DNA and 5 μg of beta-gal DNA were used for 10 cm plates. Receptors were incubated with agonist for five days. Data are the means of triplicate determinations. The lines are fits of the data to a single mass-action site of action by nonlinear regression. A chimeric construct of α2c10 was prepared using PCR and standing cloning techniques. Specifically, the entire i3 loop of the alpha2c10 was replaced with the majority of the corresponding alpha 1Ai3 loop. Beta-galactosidase was assayed after incubation in ONPG for 24 hours with absorbance read at 420 in the spectrophotometer.

Many receptors that do not mediate robust responses in amplification assays can be engineered to mediate responses by changing their selectivity for signal transduction pathways. As illustrated in FIG. 17, the ability of alpha2 adrenergic receptors to mediate functional responses can be greatly amplified by inserting the third loop of the alpha1 receptor. Alpha1 receptors efficiently couple to Gq, while alpha2 receptors more efficiently couple to Gi. As suggested by this data and others, the third loop is thought to be the primary determinant of coupling selectivity.

I claim:

1. A method for detecting a mutant form of a receptor or mutant form of a signal transducing protein associated with said receptor, which mutant form mediates cell amplification in the absence of an agonist of said receptor and which activation of non-mutant form of said receptor or non-mutant form of said signal transducing protein mediates cell amplification in the presence of, but not the absence of, an effective concentration of said agonist, comprising (a) providing a library of DNAs expected to comprise at least one DNA sequence coding for the mutant form of said receptor or mutant form of a signal transducing protein;

(b) transfecting the DNAs of step (a) into cells, said transfected cells also comprising a transfected marker of cell amplification;

(c) incubating a cell culture which comprises the transfected cells of step (b) and which also comprises non-transfected cells which do not comprise said transfected marker (i) in the absence of an agonist of said receptor or (ii) in the presence of a lower concentration of said agonist than the effective concentration required for the activation of the non-mutant form of said receptor or a non-mutated form of said signal transducing protein for a period of time sufficient to permit cell amplification of said transfected cells; and (d) determining the level of cell amplification of said transfected cells by measuring the level of marker in cell culture, increased levels of marker indicating the presence of a mutant form of said receptor or signal transducing protein in said cell culture, which mutant form mediates cell amplification in the absence of an agonist of the receptor or in the presence of a lower concentration of said agonist than the effective concentration required for the activation of the non-mutant form of said receptor or a non-mutated form of said signal transducing protein.

2. The method according to claim 1, wherein the mutant form is associated with a disease state.

3. The method according to claim 1, wherein the mutant form is mutated m5 nicotinic acetylcholine receptor.

4. The method according to claim 1, wherein the DNA transfected into the cell comprises an oncogene.

5. The method according to claim 1, wherein the transfected marker is DNA coding for said receptor or mRNA transcribed thereby, DNA coding for an enzyme, DNA coding for a binding protein or DNA coding for an antigen.

6. The method according to claim 1, wherein the transfected marker is DNA coding for an enzyme selected from the group consisting of phosphatases, beta-galactosidase, urease, glucose oxidase, carbonic anhydrase, acetylcholinestsse, glucoamylase, malate dehydrogenase, glucose-6-phosphate dehydrogenasce, beta-glucosidase, proteases, pyruvate decarboxylase, esterases, luciferase, alcohol dehydrogenase, and peroxidases.

7. The method according to claim 1, wherein the transfected marker is DNA coding for an acid phosphatase or alkaline phosphatase.

8. The method according to claim 1, wherein the transfected marker is DNA coding for horseradish peroxidase.

9. The method according to claim 1, wherein the transfected marker is DNA coding for beta-galactosidase.

10. A method for detecting a mutant form of a receptor or mutant form of a signal transducing protein associated with said rector, which mutant form mediates cell amplification in the absence of an agonist of said receptor and which activation of non-mutant form of said receptor or non-mutant form of said signal transducing protein mediates cell amplification in the presence of, but not absence of, an effective concentration of said agonist, comprising (a) providing a library of DNAs coding for a given receptor or signal transducing protein associated with said receptor, said library being expected to comprise at least one DNA sequence coding for the mutant form of said receptor or mutant form of said signal transducing protein;

(b) transfecting the DNAs of step (a) into cell culture, said transfected cell culture also comprising a transfected DNA coding for a marker enzyme of cell amplification;

(c) dividing the cell culture of step (a), the cell culture comprising transfected cells comprising said marker enzyme and nontransfected cells not comprising said marker enzyme into several identical aliquots, (d) incubating each aliquot with one or more test substances for a period of time sufficient to permit cell amplification of said transfected cells and hereby distinguish between the mutant and wild-type form of the protein, and (e) determining any change in cell amplification by measuring marker enzyme activity in each aliquot, increased levels of marker indicating the presence of a mutant form of said receptor or signal transducing protein in said cell culture, which mutant form mediates cell amplification in the absence of an agonist of the receptor.

11. The method according to claim 10, wherein the marker enzyme is select from the group consisting of phosphatases, beta-galactosidase, urease, glucose oxidase, carbonic anhydrase, acetylcholinesterase, glucoamylase, malate dehydrogenase, glucose-6-phosphate dehydrogenase, beta-glucosidase, proteases, pyruvate decarboxylase, esterases, luciferase, alcohol dehydrogease, and peroxidases.

12. The method according to claim 10, wherein the mutant form of the receptor is a mutated m5-receptor, mutated m5 muscarinic acetylcholine receptor.

13. The method according to claim 10, wherein the marker enzyme is beta-galactosidase.

* * * * *